United States Patent [19]

Hayden et al.

[11] Patent Number: 5,534,438
[45] Date of Patent: Jul. 9, 1996

[54] PROCESS FOR ISOLATING GENES AND THE GENE CAUSATIVE OF HUNTINGTON'S DISEASE AND DIFFERENTIAL 3' POLYADENYLATION IN THE GENE

[75] Inventors: Michael Hayden; Paul Goldberg; Susan Andrew, all of Vancouver; Johanna M. Rommens, Willowdale, all of Canada

[73] Assignees: University of British Columbia, Vancouver; HSC Research & Development Ltd., Ontario, both of Canada

[21] Appl. No.: 126,587

[22] Filed: Sep. 24, 1993

[30] Foreign Application Priority Data

Mar. 25, 1993 [CA] Canada .................................. 2092455

[51] Int. Cl.$^6$ ............................ C12N 15/12; C12N 15/63
[52] U.S. Cl. .................... 435/320.1; 536/23.5; 536/24.3; 536/24.31
[58] Field of Search .............................. 536/24.3, 24.31, 536/23.5; 435/320.1

[56] References Cited

PUBLICATIONS

MacDonald, M. E., et al. (1993) Cell 72, 971–983.
Hutchinson, G. B., et al. (1993) Nuc. Acids Res. 21(15), 3379–3383.
Goldberg, Y. P., et al. (1993) Nature 362, 370–373.
Goldberg, Y. P., et al, (1992) Hum. Mol. Genet. 1(9), 669–675.
Snell, R. G., et al. (1993) Hum. Mol. Genet. 2(3), 305–309.
Buckler, A. J., et al. (1991) Prod. Natl. Acad. Sci. USA 88, 4005–4009.
MacDonald, M. E., et al. (1991) Am. J. Hum. Genet. 49, 723–734.
J. M. Rommens et al.; "A Transcription Map of the Region Containing the Huntington Disease Gene", Human Molecular Genetics; 1993 vol. 2, No. 7, pp. 901–907.
Alan B. Sachs, "Messenger RNA Degradation in Eukaryotes", Cell; 74:413–421 (1993).

Primary Examiner—Charles L. Patterson, Jr.
Attorney, Agent, or Firm—Bell, Seltzer, Park & Gibson

[57] ABSTRACT

The underlying genetic defect of Huntington disease (HD) has been mapped to chromosomal band $4_p16.3$. Refined localization using recombinant HD chromosome analysis and allelic association analyses have identified two distinct candidate regions. Using a cDNA hybrid selection procedure, α-adducin has been mapped to the proximal 2.2 Mb 4D gene candidate region within 20 kb of D4S95. Several clones have been mapped within the minimal region containing the HD gene. The clones GT 70 and GT 149 are particularly useful in detecting changes in this portion of the gene of HD patients.

13 Claims, 23 Drawing Sheets

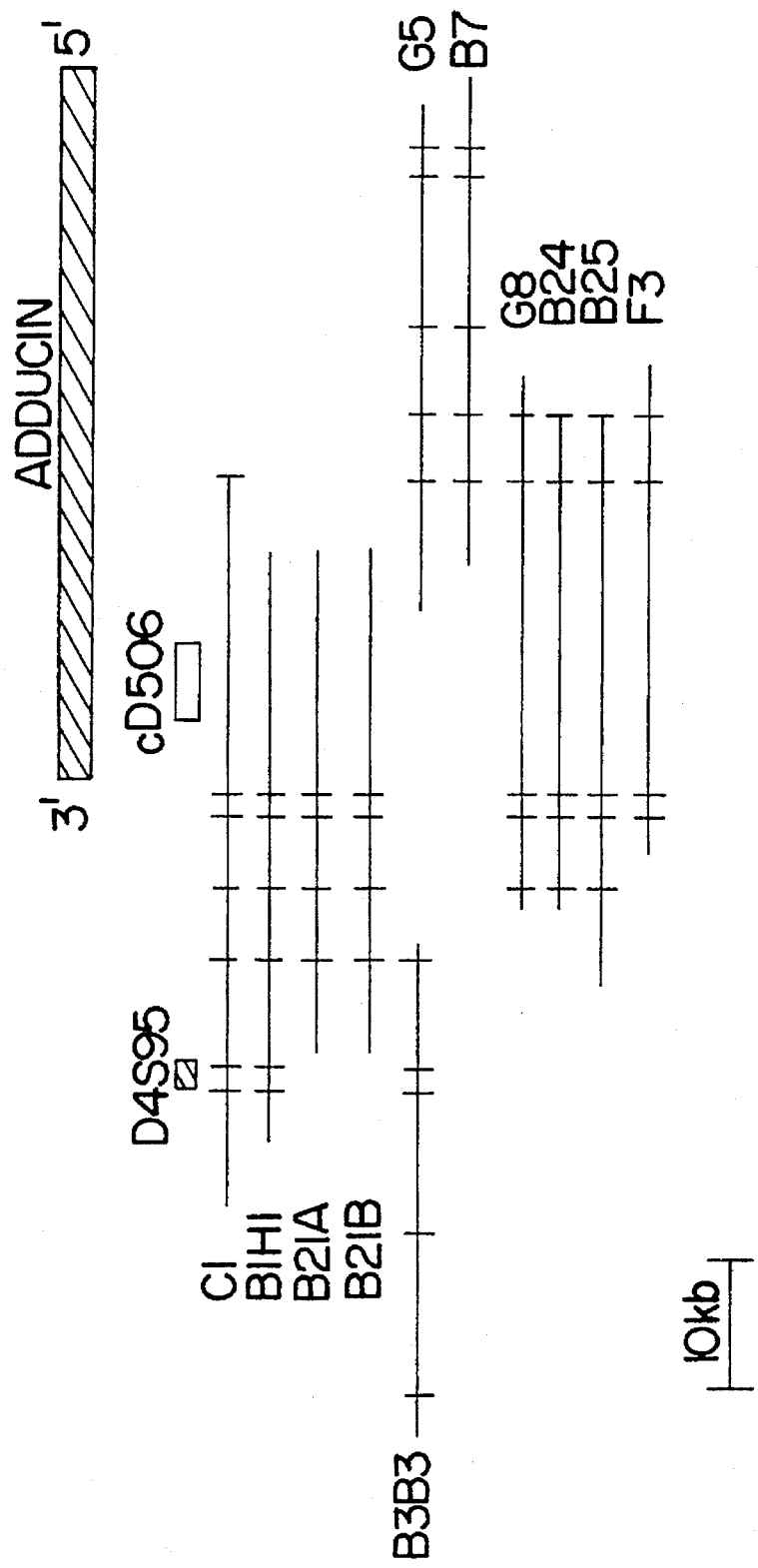
FIG. IA.

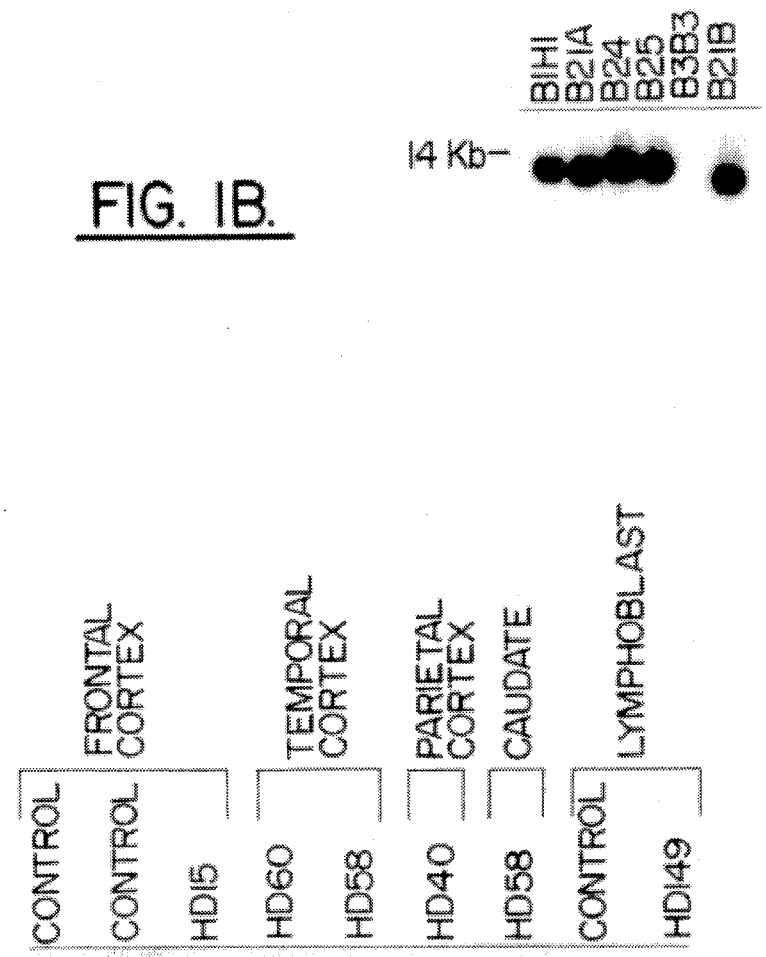
FIG. 1B.
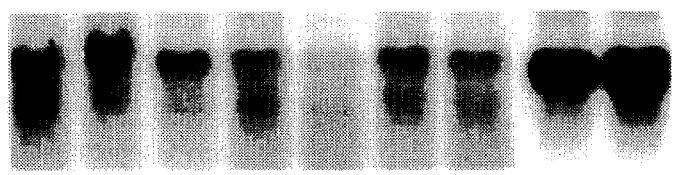
FIG. 2A.
FIG. 2B.
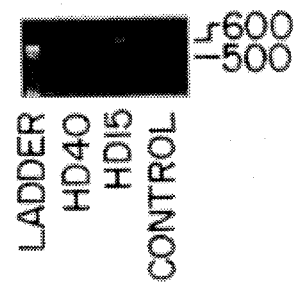
FIG. 3A.

SEQUENCE OF exon-A:
bp 1567
     *
```
ACT AAG CTG TGG ACG AAC ATT ACA CAC GAT CAC GTG AAA CCC TTG CTG
TGA TTC CAC ACC TGC TTG TAA TGT GTG CTA GTG CAC TTT GGG AAC GAC
 T   K   V   W   T   N   I   T   H   D   H   V   K   P   L   L
```
CODON 471

```
CAG TCT CTC TCG TCC GGT GTC TGC GTG CCA AGC TGT ATT ACC AAC TGC
GTC AGA GAG AGC AGG CCA CAG ACG GGT TCG ACA TAA TGG TTG ACG
 Q   S   L   S   S   G   V   C   V   P   S   C   I   T   N   C
```

```
TTG TGG ACT
AAC ACC TGA
 Q   S   L
```

SEQUENCE OF exon-B:
bp 2015
     *
```
GAG GAA GGA GAC GGA TGC GCT AGA GAG TAC CTG TTA CCC TAA CCT TGT
CTC CTT CCT CTG CCT ACG CGA TCT CTC ATG GAC AAT GGG ATT GGA ACA
 E   E   G   D   G   C   A   R   E   Y   L   L   P   *   P   C
```
CODON 621

FIG. 3C.

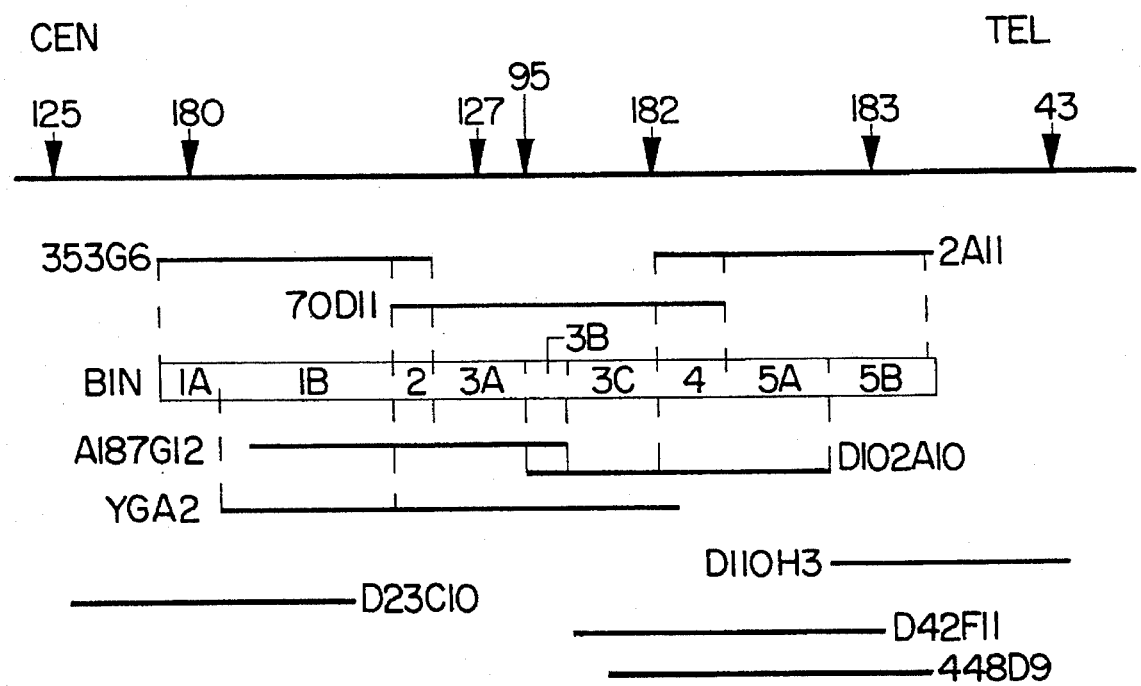
FIG. IIA.

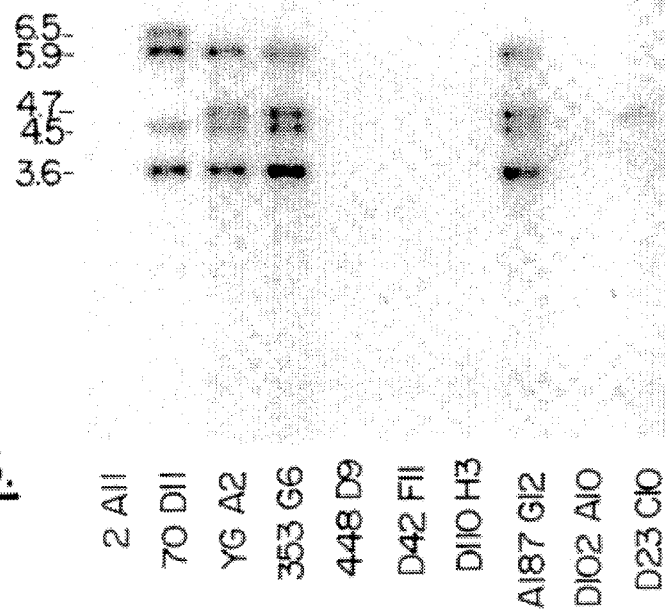
FIG. IIB.
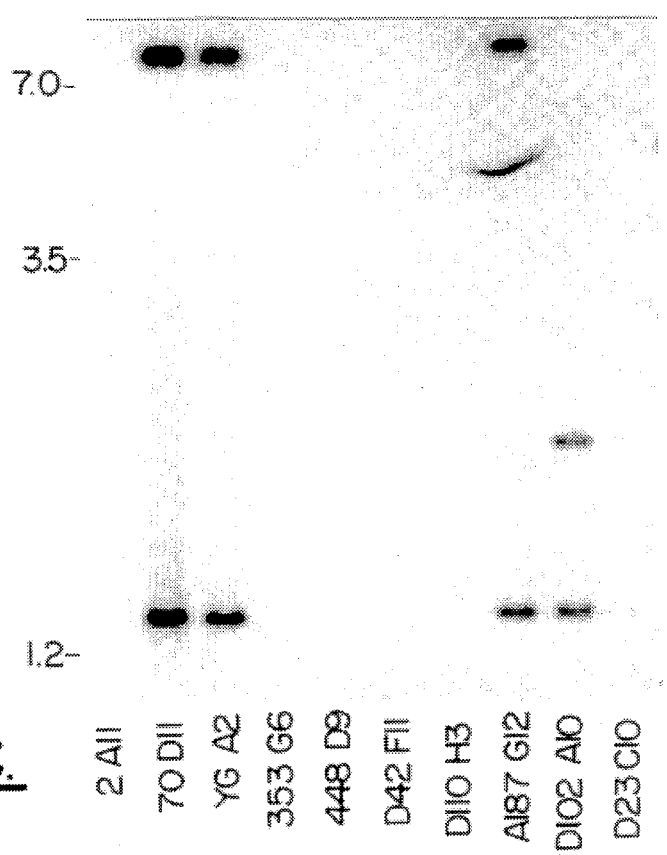
FIG. IIC.

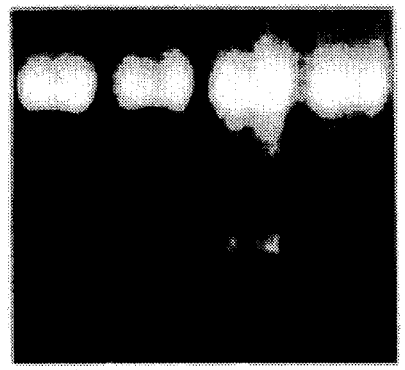
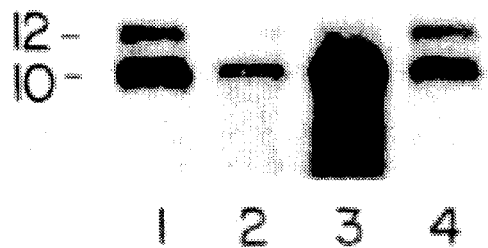
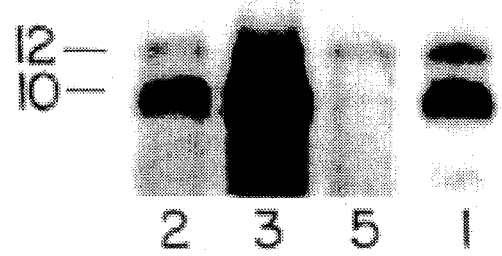
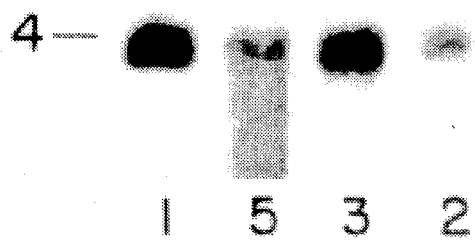
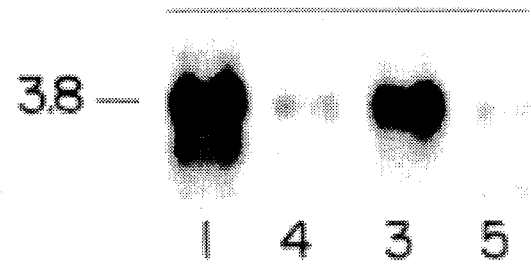
FIG. 12.

GT70
```
  1 AAAGGAAATT AAAAAGAATG GTGCCCCTCG GAGTTTGCGA GTGCCCCTGT GGAGGTCTGC
 61 TGAGCTGGCT CACCTGGTTC GGCCTCAGAA ATGCAGGCCT TACCTGGTGA ACCTTCTGCC
121 GTGCCTGACT CGAACAAGCA AGAGACCCGA AGAATCAGTC CAGGAGACCT TGGCTGCAGC
181 TGTTCCCAAA ATTATGGCTT CTTTTGGCAT TTGCAAATGA CAATGAAAGG TTGTTAAAGG
241 CCTTCATAGC GAACTGAAGT CAAGCNNCCC CCACCATTCG GCGGACAGCG GCTGGATCAG
301 CAGTGAGCAT CTGCCAGCAC CAAGAAGGA CACATATTT CTATAGTTGG CTACTAAATG
361 TGCTCTTAGG CTTCNCGTTC TCAAGAAGGA TGAACACTCC ACNTGCTGAT TCTTGGGTG
421 CTGCTCACCT TGAGGTATTT CTGTCGAGGA CTGCAGCAGC AGGTCAAGGA CAQAAGCCTG
481 AAAGGAGTCT TCGGAGTGAC GTGCCCTTG AGGAAAGAA TCCTTCTGCA GAGCACTTGA
541 TCCAGGTTTA TGAACTGACG TTACATGATA CACAGCACCA AGACCACAAT GTTGTGACCG
601 GAGCCCTGGA GCTGTTGCAG CAGCTCTTCA CACAGCACCA ACCCGAGCTT CTGCAAACCC
661 TGACCGCAGT CGGGGGCATT GGACGCCTCA GAACGCCTCC ACCACCTTGACC GGTGGCCGAA
721 GCCGTAGTGG GAGTATTGTG GAACTTATAG CTGGAGG
```

GT149
```
  1 GGCCATTTG AGGGTTCTGA TTTCCCAGTC AACTGAAGAT ATTGTTCTTT CTCGTATCAG
 61 GAGCTCTTCT TCTCTCCGTA TTTAACTCCT GTACAGTAA TAATAGGTTA AGAGATGGGG
121 ACAGTACTTC AACNCTAGAA GAACACAGTG AAGGGAAACA AATAAAGAAT TTGCCAGAAG
181 AAACATTTTC AAGGTTTCTA TTACAACTGG TTGGTATCTT TTAGAAGACA TTGTTACAAA
241 ACAGCTGAAG GGTGGGAAAT GAGTGAGCAG CAACATACTT TTTATTGCCA GGAACTAAGG
301 CACACTGCTA ACGTGTCTGA TCCACATCTT CAAGTCTGGA ATGTTCCGGA GAATCACAGC
361 AGCTGCCACT AGGCTGTTCC GCAGTGATGG CCATGATCAC CTGTGGCGGC CCCTGGACAG
421 CTGGAACTTG CGGGCTCGTT CCATGATCAC CACCCACCCG CACCCACCTG TGGTCTGGTG
481 TCAGATACTG CTGCTTGTGA AGGAGACCGA CTACCGCTGG TGGGCAGAAG TGCAGCAGAC
541 CCCGAAAAGA CACAGTCTGT CACAGCACAA GTTACTTAGC CCAC
```

FIG. 13.

```
HD14          GCAGCCCCAGGAAGCCCATATCACCGGCTGCTGACTTGTTACGAAATGTCCACAAGGTCACCACCTGC  9747
HD12          GCAGCCCCAGGAAGCCCATATCACCGGCTGCTGACTTGTTACGAAATGTCCACAAGGTCACCACCTGC
AMINO ACID     A  P  G  S  P  Y  H  R  L  L  T  C  L  R  N  V  H  K  V  T  T  C

HD14-UTR      TGAGGCCATGGTGGGGAGAGACTGTGAGGGGCAGCTGGGGGCCGGAGCCTTTGGAAGTCTGTGCCCTTGT  9817
HD12-UTR      TGAGGCCATGGTGGTGGGGAGAGACTGTGAGGGGCAGCTGGGGGCCGGAGCCTTTGGAAGTCTGTGCCCTTGT
                  *

HD14-UTR      GCCCTGCCTCCACCGAGCCAGCTGGTCCCTATGGGCTTCCGCACATGCCAGGAGCCTGGGCCAGGCAACGTG  9887
HD12-UTR      GCCCTGCCTCCACCGAGCCAGCTGGTCCCTATGGGCTTCCGCACATGCCAGGAGCCTGGGCCAGGCAACGTG

HD14-UTR      CGTGTCTCTGCCATGTGGCAGAAGTGCTCTTTGTGGCCAGGCAGGAGTGTCTGCAGTCCTGGT  9957
HD12-UTR      CGTGTCTCTGCCATGTGGCAGAAGTGCTCTTTGTGGCCAGGCAGGAGTGTCTGCAGTCCTGGT

HD14-UTR      GGGGCTGAGCCTGAGGCCTTCCAGAAAGCAGGAGCAGCTGTGCTGCACCCATGTGGGTGACCAGGTCCT  10027
HD12-UTR      GGGGCTGAGCCTGAGGCCTTCCAGAAAGCAGGAGCAGCTGTGCTGCACCCATGTGGGTGACCAGGTCCT

HD14-UTR      TTCTCCTGATAGTCACCTGTGGCTGTTGCCAGTTGCCAGCTGCTCTTGCATCTGGGCCAGAAGTCCTCC  10097
HD12-UTR      TTCTCCTGATAGTCACCTGTGGCTGTTGCCAGTTGCCAGCTGCTCTTGCATCTGGGCCAGAAGTCCTCC

HD14-UTR      CTCCTGCAGGCTGGGGTCCTGTTGGCCTCTGCTGTCCTGCAGTAGAAGGTGCCGTGAGCAGGCTTTGGGAAC  10167
HD12-UTR      CTCCTGCAGGCTGGGGTCCTGTTGGCCTCTGCTGTCCTGCAGTAGAAGGTGCCGTGAGCAGGCTTTGGGAAC

HD14-UTR      ACTGGCTGGCTCTCCCCGGTGTGCATGCCACGCCCCGTGTCTGATGCCATGGCCT  10237
HD12-UTR      ACTGGCTGGCTCTCCCCGGTGTGCATGCCACGCCCCGTGTCTGATGCCATGGCCT

HD14-UTR      GTGCTGGGCCAGTGGCTGGGGTGCTAGACACCCGGCACCATTCCCTCTCTTTTCTCTCAGGAT  10307
HD12-UTR      GTGCTGGGCCAGTGGCTGGGGTGCTAGACACCCGGCACCATTCCCTCTCTTTTCTCTCAGGAT

HD14-UTR      TTAAAATTTAATTATATCAGTAAAGAGATTAATTTTAACGTAACTCTTTCTATGCCCGTGTAAAGTATGT  10377
HD12-UTR      TTAAAATTTAATTTATATCAGTAAAGAGATTAATTTTAACGTAAAAAAAAAAAAAAAAAAA

FROM FIG. 15B.

```
TTGTTGCAAATGTGATTAATTTGGTTGTCAAGTTTTGGGGTGGGCTGTGGGGAGATTGCTTTTGTTTC
CTGCTGTAATATCGGGAAAGATTTCCCTTCCGCTGCCTTAATGAAACCAGGGTAGAATTGTTGGCAAT
TTCCTTTCCCAAATGTCCTTTGTTACTGTTCTTCCACCCAGAATGTAGAGCTCGAGTCTATGTCCTTT
CCAAGTGCTCCTTCCCAGACACGGGGAGCTCGGGGTCATTTCAGGAAGCCCATGAAGGCCAATGAACT
AGCTGAACTCTTCATGGAACTTTCCCAGACACGGGGAGCTGGGGAGCTCCTGCCAGGGACAGCCAATGAACT
CCCCATCTTCATGACGTTCCCGTGAGCCAAGATAGTTCTGATAGAACGGATAGTTAGTTCTATCGGAC
AGATGAGCCCCATCTCATGACGTTCCCGTGAGCCATCCTCAGGGATGAGTCAAGCTGGACTTTCTGTG
TGGAACTTACCCTGTGAGCTTGGAACTTCCCAGACAGGGTAGAGGCTGAAGGGAGACCTTGCTGGACTTTCTGTG
CTTGCCGGGAGGAGTGAGAGAAGAAGGGGGTTCAGGAGAGATCTTGAGAGCTGGAAGGAGGCATGCCTCAGGGTAGACATG
TGTAGGGACACTCGCTTGGAAGGTTCAGGGCCAAGATCTTGAGAGCTTGGGAGGAGGCTCCCGCATGCCTCAGGGGACT
GAAGGCAACCCCTCTGGAAAGTTCAGGGCCAAGTTGTTTGCACCTGGACTTGGGTAACTCTGTTGCCAGCCT
AACGCCTTCCCCTCAGTTGTTCTAAGAGCAGAGAGATCTCCCGCCAAGTCCCCAAGTCTCTGAGCTTGAGCTTGGTAACTCTGTTGCCAGCCT
GGAGGATCGTGGCCAACCGGTGAGCCTACGGGGACCTTGGCCAGTTTCTAAGAGCAGAGGACTGCCAGCCTCCTTGCCAAGGCCA
GGTCTCACTGCCTTTGCACCTGGCTGGGTCAGCTGAATGCTTCTGAGAGCAAAGGGAAGACTGACGA
CTGTGATGTATTTAATTTTTAAACTGCTGCAAAAAAAAAAAAAAAAAAAGAGAGCTTGTACATCCAAATTAAAGGGAAAAAATGGAAACC
ATCAAAAAAAAAAAAAAAAAAAAAAAAAA
```
13710

FIG. 15C.

PCR PRIMER
P1 SEQUENCE: TCAGGGCAGGGCTCATTCATTC
P2 SEQUENCE: GATGTACAATGTTTGCAGCAGTTA

P: Pst I SITE, H: Hind III SITE.

PROCESS FOR ISOLATING GENES AND THE GENE CAUSATIVE OF HUNTINGTON'S DISEASE AND DIFFERENTIAL 3' POLYADENYLATION IN THE GENE

FIELD OF THE INVENTION

This invention relates to Huntington Disease (HD), genetic defects causative of the disease, diagnosis of patients susceptible to the disease and techniques for identifying the HD gene.

BACKGROUND OF THE INVENTION

Huntington disease (HD) is an autosomal dominant neurodegenerative disorder usually characterized by onset in adult life with psychiatric disturbances, progressive involuntary movements and dementia. The genetic defect underlying HD has been mapped to chromosomal band $4_p$ 16.3. Allelic association studies with genetic markers and assessment of specific recombination events in affected families to further refine its location have provided conflicting results. These results place the gene either at a proximal location within a 2.2 Mb fragment or in a more distal non-overlapping DNA segment close to the telomere of $4_p$. Despite some differences in published reports of allelic association, all studies have consistently demonstrated nonrandom association between the gene causing HD and a DNA marker at D4S95 which is located in the proximal 2.2 Mb candidate region approximately 1.2 Mb telomeric to D4S10, the locus first found to be linked to HD.

The biochemical defect underlying HD is not known and therefore current strategies to identify the HD gene have necessitated assessment of genes located in both of the candidate regions. Cloning genes from these large regions has in the past been limited by the difficulties in rapidly identifying coding regions over large stretches of genomic DNA. More recently however, a variety of techniques including exon amplification and direct cDNA selection strategies have been developed which greatly facilitate the search for coding sequences in genomic DNA. We have isolated and cloned the cDNA for human brain or α-adducin gene, a portion of which was initially detected by using a modification of a direct cDNA selection strategy. This gene has been localized to within 20 kb of D4S95.

Adducin is a membrane associated cytoskeleton protein comprised of α and β subunits. Adducin in solution is a heterodimer, and is present in membranes of a wide variety of cells including erythrocytes and neurons. The erythrocyte cytoskeleton has been shown to have a lattice-like organization with actin complexes crosslinked by spectrin molecules extending throughout the entire membrane skeleton. Adducin is thought to play a role in the assembly and maintenance of the actin-spectrin junctional complex and promotes binding of spectrin to actin. Adducin was initially identified on the basis of its calmodulin binding activity which inhibits its ability to promote the binding of spectrin with actin. Furthermore, α-adducin is phosphorylated by cAMP-dependent protein kinase and is also a major substrate for protein kinase C. Brain tissue contains an isoform of adducin in lower concentration than in erythrocyte membranes but with similar properties including the association with spectrin-actin complexes, calmodulin binding and phosphorylation by protein kinase C.

The functional consequences of defects in the adducin gene are unknown. However mice deficient in ankyrin, a related cytoskeletal protein with spectrin binding properties have, in addition to hemolytic anemia, significant neurological dysfunction associated with Purkinje cell degeneration in the cerebellum and the development of a late onset neurological syndrome characterized by persistent tremor and gait disturbance. Ankyrin and adducin appear to have different functions in the membrane skeleton but both play a role in the interaction with spectrin and the maintenance of normal membrane integrity. Moreover, previous studies of red cells, fibroblasts, lymphocytes and neurons in affected HD patients have pointed to a possible generalized disturbance in membrane structure and function in this disorder.

SUMMARY OF THE INVENTION

In order to facilitate a description of various embodiments of the invention, FIGS. 13 and 15 of the Drawings show DNA sequences of GT 70, GT 149 and UTR of HD 14, respectively. A detailed description of the drawings follow hereinafter.

Many aspects of the invention may be used to develop information respecting HD. Various clones of the HD gene and surrounding DNA sequences are valuable in gene diagnosis and family studies. According to an aspect of the invention, gene clones GT 70 and GT 149 are particularly useful in detecting changes or re-arrangements in the HD gene to determine patient's susceptibility to HD.

According to another aspect of the invention the HD gene includes cDNA clones GT 70 and GT 149, as shown in FIG. 13.

Another aspect of the present invention is a novel purified cDNA molecule having the sequence equivalent to GT 70.

Another aspect of the present invention is a novel purified cDNA molecule having the sequence equivalent to GT 149.

A further aspect of the present invention is a purified DNA molecule having the sequence designated UTR of HD 14 of FIG. 15, the sequence being the 3' untranslated terminal portion of a gene associated with Huntington's Disease.

A further aspect of the present invention is a purified mRNA molecule transcribed preferentially in the human brain by transcription of said DNA molecule UTR of HD 14.

BRIEF DESCRIPTION OF THE DRAWINGS

Various aspects of the invention are demonstrated with respect to the appended figures wherein:

FIG. 1

(A) cosmid contig showing localization of α-adducin gene 20 kb distant to D4S95. An EcoRI restriction map of ten cosmids spanning approximately 85 kb obtained from the chromosome walk is shown.

(B) cD506, a probe from the 3' region of a α-adducin cDNA was hybridized to cosmids B1H1, B21A, B24, B25, B3B3, B21B. The EcoRI fragments detected in each cosmid are shown, confirming localization of α-adducin to this contig.

FIG. 2

(A) Northern blot showing a 4 kb α-adducin transcript in both control and HD patients in brain and lymphoblast. HD149 is homozygous for the HD mutation.

(B) As a control β-actin was subsequently hybridized to the same filter.

FIG. 3

(A) Ethidium bromide gel of PCR products using primer ADU1111–1615 showing the expected PCR products of 504 bp predicted from published erythrocyte α-adducin sequence and a novel band of about 600 bp containing alternately spliced exon-A.

(B) Schematic map depicting the position of alternately spliced exons of brain α-adducin. Nucleotide position according to the published sequence of erythrocyte α-adducin. (GenBank accession number X58141), is shown above the schematic and the amino acid numbering is shown below. The 93 bp exon-A is inserted in frame between codon 471–472. The 34 bp exon-B is inserted within codon 621, which disrupts the frame and introduces a stop codon after 11 novel ammo acids.

(C) The sequence of the two alternately spliced exons and their translated amino acids. The sequence of exon-A (SEQ ID NO:1) and exon-B (SEQ ID NO:3) is boxed and flanked by exonic sequence.

FIG. 4

Figure 4A:
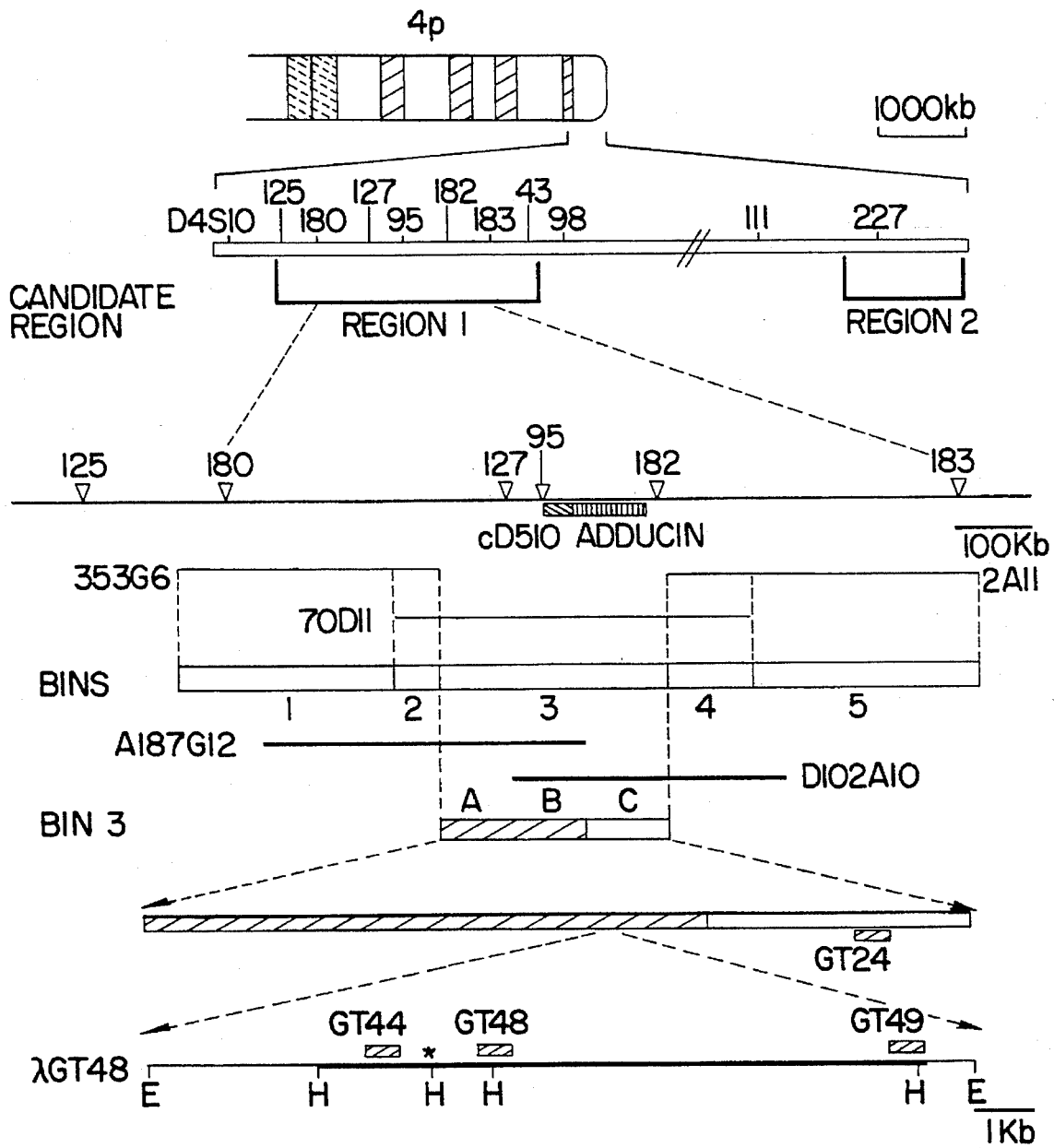
Figure 4B:
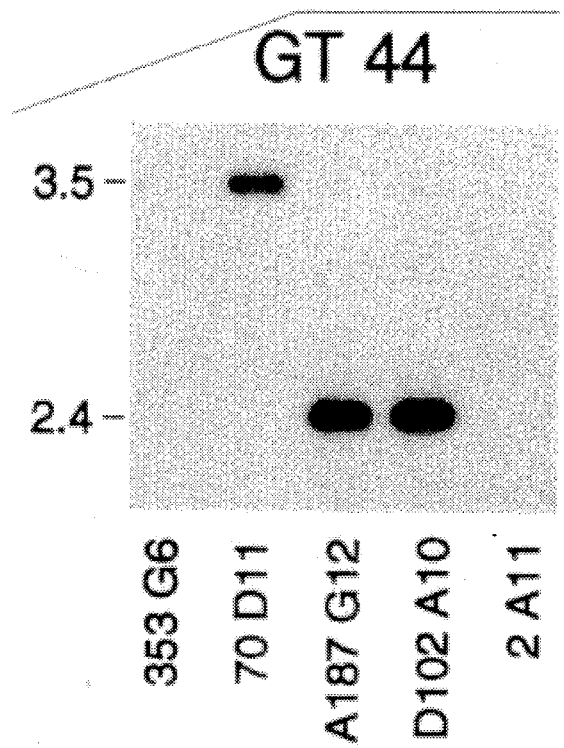
Figure 4C:
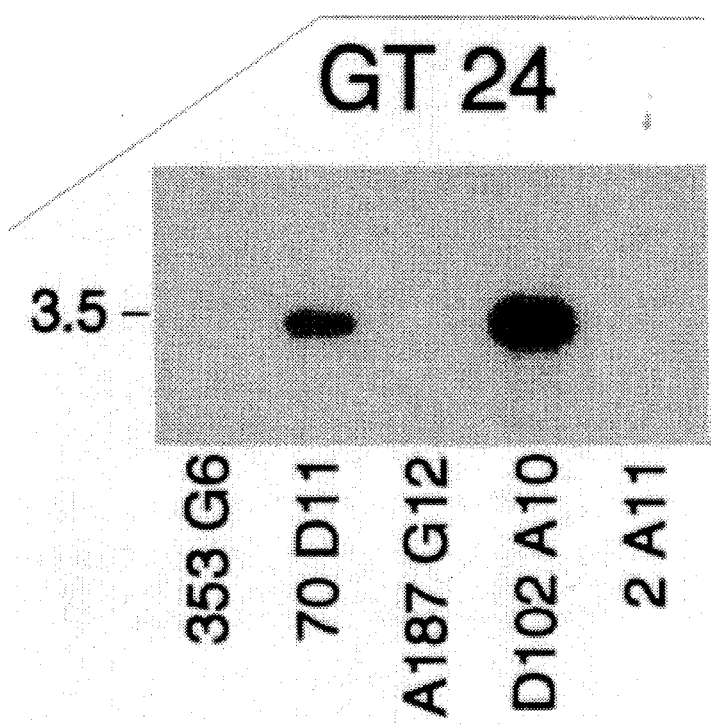

FIG. 4a. Mapping of transcriptional units within the HD candidate region. Overlapping regions with Yacs 353G6, 70D11 and 2A11 were used to define 5 separate genomic BINS. Yacs A187G12 and D102A10 were used to further refine BIN 3 into three separate compartments: A,B,C. GT clones were mapped by hybridization to digest Yac DNA and assigned to BINS accordingly. GT 44, 48 and 49 mapped to both A187G12 and D102A10, as well as 70D11. All of these clones were contained within a λ phage (λGT 48) isolated using GT 48 as a probe. λGT48 contains a HindIII polymorphism (*) detected by both GT 44 and GT 48. FIG. 4b. Yac mapping of GT 44, illustrating the HindIII polymorphism. FIG. 4c. GT 24 hybridizes only to 70 D11 and D102A10 indicating its position within BIN 3C.

FIG. 5

Recombination within a HD family refining the proximal boundary of the HD candidate region. The affected haplotype in this family is designated within the boxed region. Recombination between markers D4S125 and D4S127 in individual II-6 reduced the candidate region of the HD gene by at least 200 kb. For the markers detecting RFLPs, Southern blot analysis was performed using previously described methods and probes 10. Microsatellite repeats were detected by $32_p$-labelled PCR products resolved on a 6% denaturing polyacrylamide gel.

Northern blot analysis of GT clones. Examples of mRNAs detected with GT clones originating from the candidate HD region are shown. Total RNA from each cell line or tissue was prepared by standard procedures. The lanes represent RNA from the following sources: 1) Caco-2 intestinal cells, 1A) Caco-2 poly A+RNA, 2) HL60 cells, 2A) HL60 Poly A+, 3) lymphoblasts, 4) fibroblasts, 5) liver, 6) Cos cells, 7) frontal cortex, 8) feral brain, 10) Caco- 2 intestinal cells. RNA was separated on 1% agarose gels containing 0.6M formaldehyde and transferred onto DX (Amersham) membranes. The integrity of the RNA is shown by the ethidium bromide stained gel in the left upper panel. Clones were radiolabeled by random priming and hybridization and washing conditions were carried out as previously described. The size of the message detected with each clone is indicated in kilobases.

FIG. 7

Figure 7A:
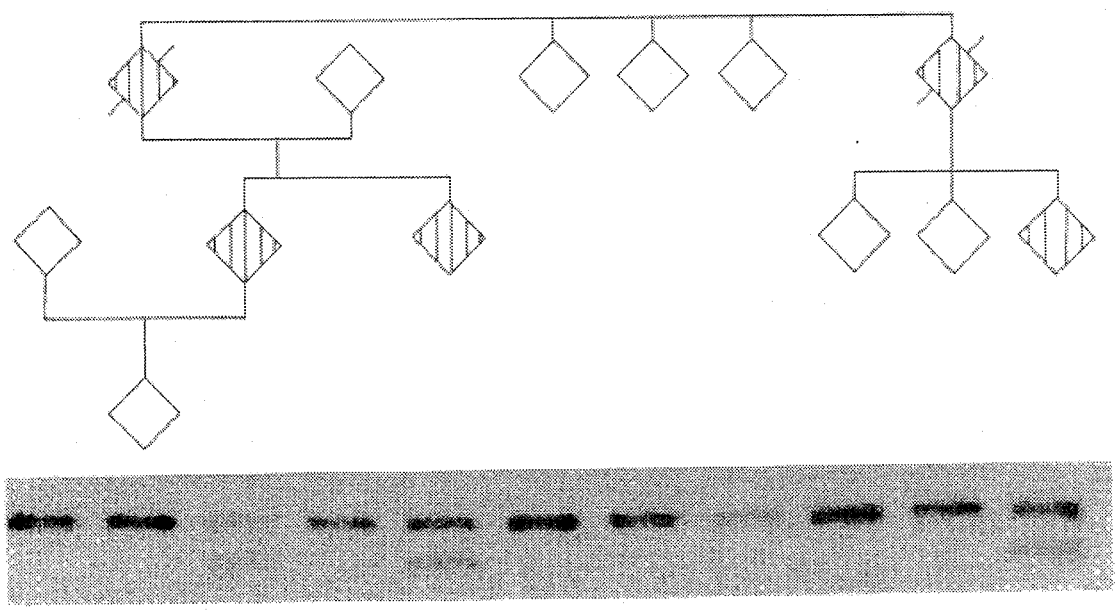
Figure 7B:
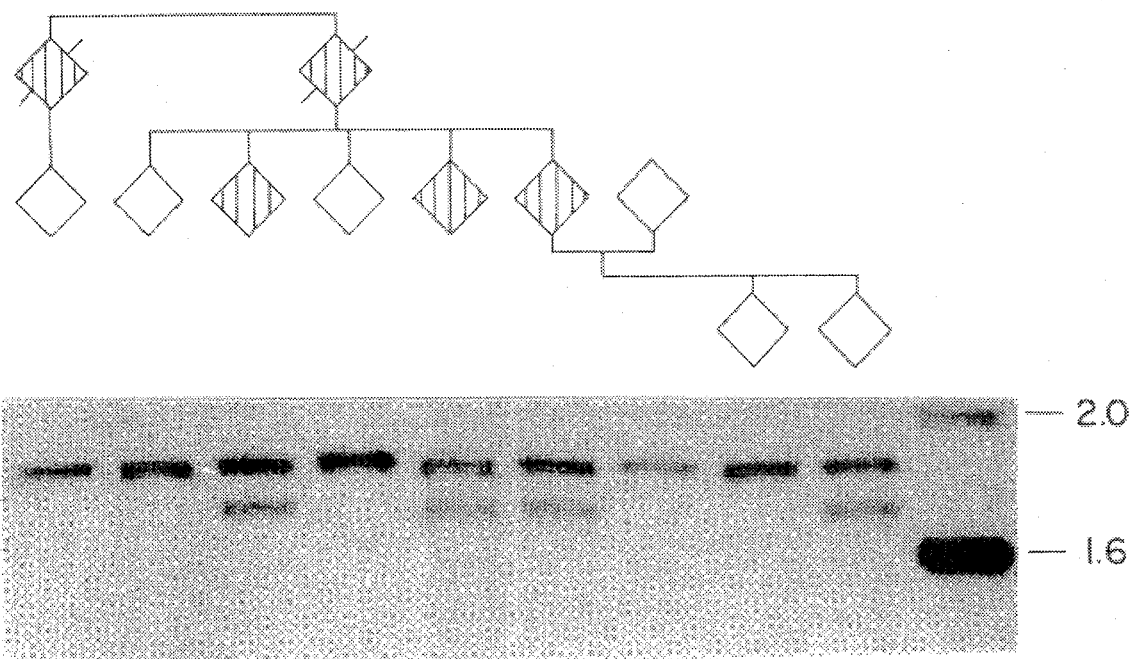
Figure 7C:
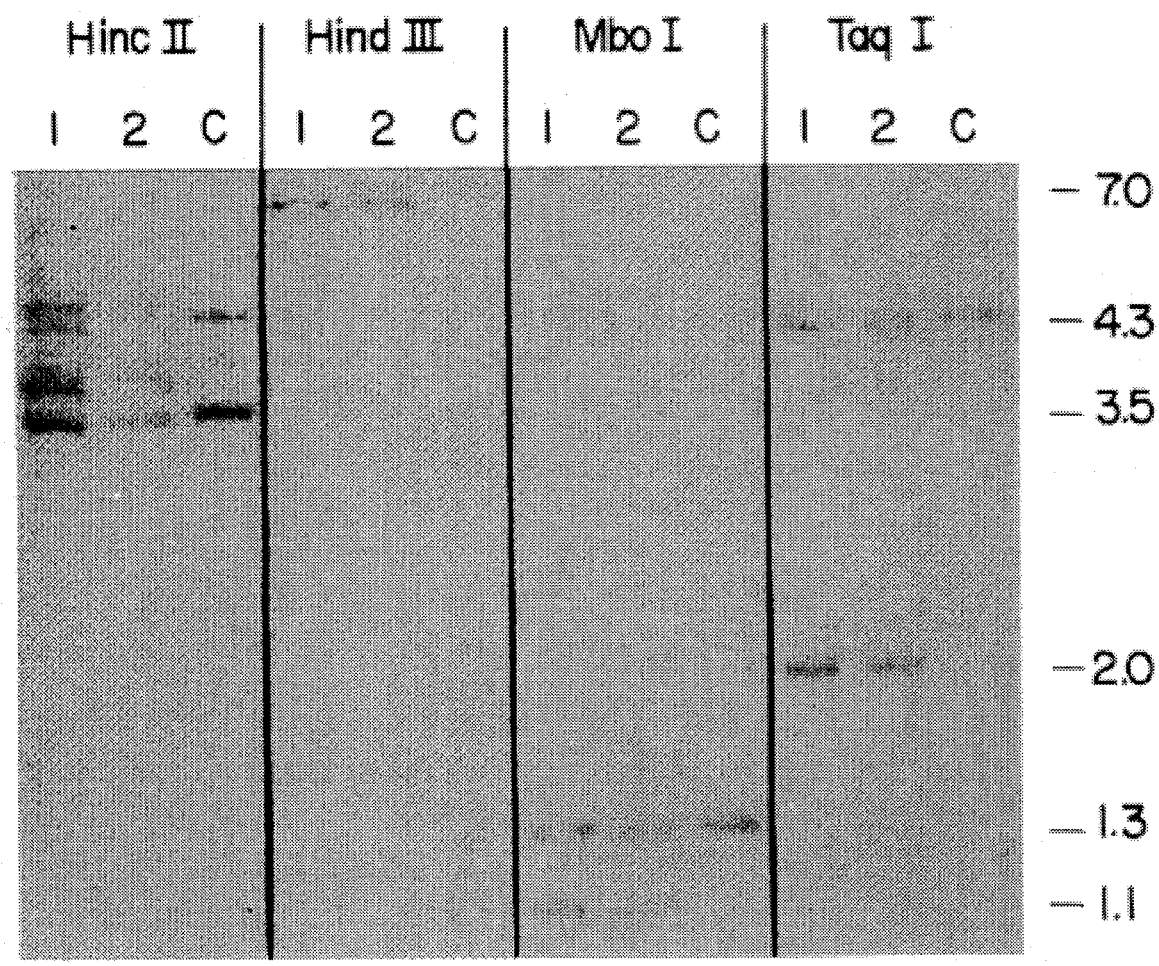

Genomic rearrangement in two families with HD. Southern blot analysis of Msp I digested genomic DNA probed with GT 48 revealed an altered band in 2 of 250. FIGS. 7a and 7b show co-segregation of the altered 1.7 kb Msp I fragment with all affected individuals in both families. FIG. 7c Southern blot analysis of genomic DNA from one affected individual from each family (lanes 1 and 2) and a control (lane C). Genomic DNA digested with a variety of enzymes and probed with GT 48 resulted in altered bands identical in the affected individuals from the two families.

FIG. 8

Figure 8A:
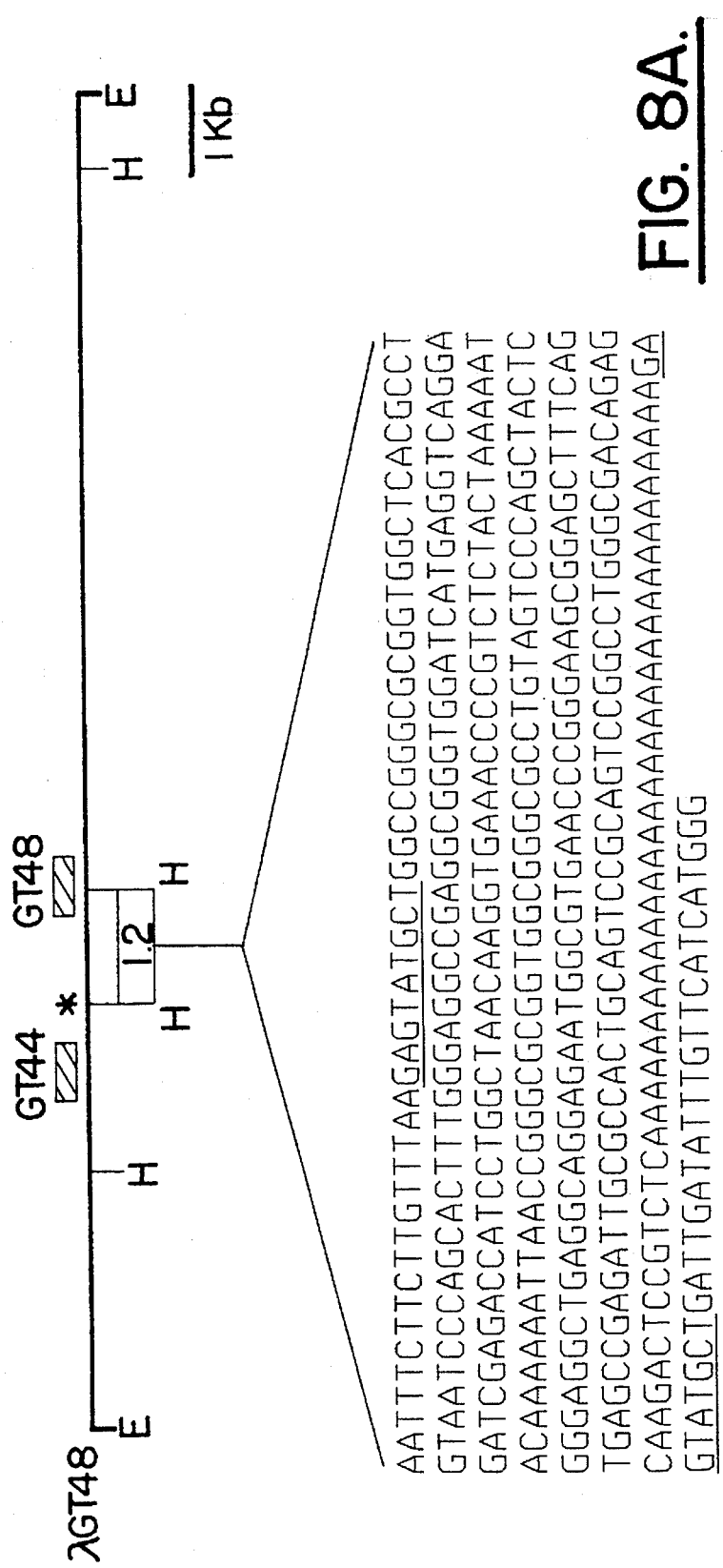
Figure 8B:
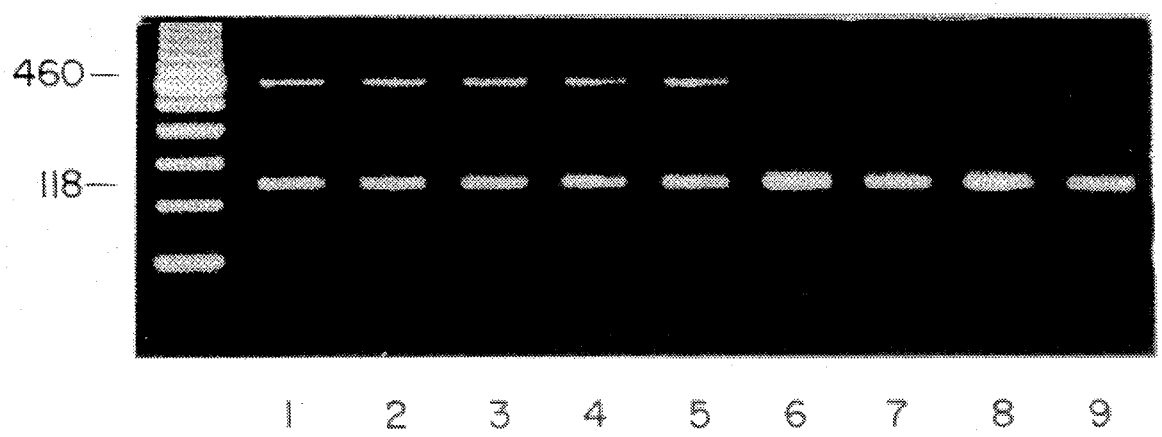

Alu retrotransposition within the HD candidate region. Mapping of the genomic region around GT 48 in controls and the affected individuals, localized the rearrangement to the 1.2 kb HindIII fragment on λGT48 (boxed). The 1.2 kb Hind III fragment (SEQ ID NO:5) was subcloned, sequenced and PCR primers spanning the insertion site were derived. These primers (A:ATGTAATTGTTCACGACAT-GTGGC (SEQ ID NO:13), B:AAATAACATCCAGAATCT-TCAGAT) (SEQ ID NO:14) generated a 118 base pair fragment in normal individuals (FIG. 8b lanes 6–9) and 460 base pair product in five affected individuals from both families (FIG. 8b lanes 1–5). The 460 base pair PCR product was subcloned (TA cloning, Invitrogen) and sequenced by ABI automated sequencing. The inserted sequence represents a full length Alu element (bold) and the insertion site is flanked by a 9 base pair direct repeat (underlined).

FIG. 9

Physical Map between D4S95 and D4S182: Long range physical mapping localized GT 24, GT 48 and the α-adducin cDNA clone to the same 60 kb Not I fragment. Cosmids J7 and B7 were isolated from a chromosome 4 specific library with D4S182 and α-adducin cDNA respectively. λGT48 and λGT24 were isolated from a λ phage library using their respective GT clones. λgt48 and λSS2 form a contig overlapping with cosmid B7. An oligonucleotide from the 5' UTR of adducin detected the D4S182 cosmid J7 as well as λGT24. By physical mapping GT 48 is approximately 20 kb from GT 24.

FIG. 10

Outline of strategy to generate transcription map of proposed region for Huntington disease. Direct selection of cDNAs from four tissues was applied to 3 YACs with minimal overlap that span a 1 Megabase region of genomic DNA around the D4S95 locus. The hybridized cDNA fragments were retrieved, cloned and verified to have originated from the starting YACs. A total of 58 cDNA fragments were placed onto the physical map using additional overlapping YAC clones. They were assembled into transcription units by hybridization to RNA and subjected to sequence analysis.

FIG. 11

Assignment of cDNA fragments to BINs by hybridization to overlapping YAC clones in the proposed region for the Huntington disease gene (A). The physical intervals defined by overlapping regions of 10 YAC clones are indicated as BINs. Each cDNA fragment was hybridized to all or a subset of the overlapping YACs such that they could be assigned to the defined regions. Two cDNA fragments (B) GT 70 and (C) GT 48 are shown hybridized to overlapping YACs digested with HindIII.

FIG. 12

RNA hybridization analysis of 5 retrieved cDNA fragments from the candidate region. An ethidium bromide stained gel is shown in the upper left panel. The clone names, their physical interval (BIN) assignment and the size of the mRNAs that were detected (in kilobases) are indicated. Hybridization to RNA from Caco-2 (intestinal), HL60, Lymphoblast, Fibroblast cell lines or from frontal cortex RNAs are shown. Part of the analysis with GT 70 has been shown previously, but sizes of the bands have been reassessed.

FIG. 13

Sequence analysis of GT 70 and GT 149. Two of the retrieved clones detected a pair of large transcripts by hybridization to RNA. These clones did not overlap and were mapped to adjacent physical intervals defined by the overlapping YACs. They contained multiple exons, demonstrated strong cross species conservation and upon sequencing analysis displayed significant coding potential (underlined). In the listings, the letter "n" designates an unidentified nucleotide.

FIG. 14

An illustration of identified cDNAs and their nucleotide positions corresponding to the HD sequence, GT 63, 70 and 149 are the fragments of the gene initially identified by gene tracking.

FIG. 15

Sequence alignment of the coding and 3' untranslated region of HD 12 (SEQ ID NO:9) and HD 14 (SEQ ID NO:8). The coding sequence of HD 12 and HD 14 is identical to the HD sequence. HD 12 ends at position 10,366. However, HD 14 cDNA shows that has an additional 3360 bp of 3' UTR sequence. Putative polyadenylation sequences are underlined.

FIG. 16

Alignment restriction sites of 3' UTR of HD 14 with cosmids at 3' end of HD gene. PstI and HindIII fragments of the 3' UTR of HD 14 are identical to that of cosmids L113B6 and L134B9.

FIG. 17

RNA hybridization of 4 cDNA fragments

A: An ethidium bromide stained gel shows the integrity of the RNA. Each lane contains 10 μg of poly $A^+$ RNA.

A1. Hybridization of GT 70 to poly $A^+$ RNA from fetal brain and CaCO-2 (intestinal) cell line and to total RNA from CaCO-2 and Hep G2 cell lines reveals 2 transcripts with the larger transcript most predominant in brain and the smaller more abundant in the cell lines.

A2. Hybridization of the same filter with 1.4 kb EcoRI/Pst fragment from the unique 3' UTR of HD 14 detects only the larger transcripts in all samples.

FIG. 17B

An ethidium bromide stained gel shows the integrity of the RNA. Each lane contains 10 μg of poly $A^+$ RNA.

B1. Hybridization of HD 14 to poly $A^+$ RNA from fetal and adult brain and to total RNA from lymphoblast and CaCo-2 cell lines.

B2. Hybridization of the unique 2.4 kb Hind III fragment from the 3' UTR or HD 14 detects only the larger transcript.

DETAILED DESCRIPTION OF THE PREFERRED EMBODIMENTS

The genetic defect underlying HD has been mapped to chromosomal band $4_p16.3$. Analysis of recombinations in separate affected families has defined the location of the defect to a 2.2 megabase interval. The distal boundary of this region involves a cross over between D4S98 and D4S43 while the proximal boundary is defined by a cross over between D4S 10 and D4S125 (See FIG. 1). A recently described recombination event distal to D 4S125 further reduced this interval and is consistent with additional genetic studies that have shown nonrandom allelic association between markers at the D4S127 and D4S95 loci and the HD gene.

Using a modified direct cDNA selection procedure we have identified the α-adducin gene from cosmids at the D4S95 locus. We have extended this effort to identify genes in a 1 megabase region surrounding the D4S95 and D4S127 loci to systematically build a transcription map of this region for HD. The direct selection or gene tracking methodology is appealing as transcribed sequences from genomic DNA that can be rapidly and directly assessed by sequence analysis are obtained. Both untranslated and exonic sequences are retrieved and furthermore, the sub-cloning of large genomic clones is not required. cDNAs of single and mixtures of up to four tissue sources were used to detect a minimum of nine transcribed regions over 1 megabase of genomic DNA in the HD proximal region. One of these transcription units correspond to the α-adducin gene.

In spite of the limitation of using only four tissue sources, the combined length of the transcripts detected with the GT clones contained within the 70D11 YAC comprising 450 kilobases of genomic DNA adds to greater than 30 kilobases, indicating that a minimum of 7% of genomic DNA in this region is transcribed. This corresponds to the overall expected proportion of transcribed sequence, but in all likelihood does not correspond to all the genes in this region.

A number of cDNA clones were obtained that did not detect mRNAs by analysing total RNA of the source tissues. However, sequence analysis and their hybridization patterns strongly suggested that these clones were portions of genes. For example, GT 133, in BIN 4, detects multiple exons on genomic DNA but did not detect a message in total RNA from the tissues tested.

Our experience with direct selection has indicated that using mixed pools of tissue yields the highest numbers of clones which map back to the original genomic DNA. To build transcription maps with mixed tissue cDNA pools one could readily retain the information of the tissue source by the incorporation of sequence specific "flags" into the oligonucleotide used to prepare the first strand of cDNA (see Methods). Also inclusion of cDNA prepared from total RNA permits proportionally more of the non-specific background clones which frequently contain rRNA sequences to be eliminated in the pre-screening step (see Methods) with total cDNA. Labelled cDNA prepared from total RNA more accurately represents repetitive sequence that is found in transcribed sequences as compared to using total human genomic DNA or Alu of Kpn specific probes. The possibility of elimination of correct cDNAs derived from very abundant messages has not proven to be a problem as illustrated by the selected clones that were shown to be derived from the α-adducin gene. These were not elated by the pre-screening procedure in spite of the high abundance of the mRNA for this gene.

With cDNA selection, map positions of the identified transcripts are dictated by the original genomic clone used, the transcription unit framework that is generated by mapping the selected cDNA clones provides a foundation with which to build a complete gene map. Additional transcriptional unit information can readily be added using cDNAs derived from other tissues or that have been detected through alternate routes. Furthermore clones that are obtained even through a single application of the selection procedure are suitable for physical mapping as they provide probes from multiple points across the entire YAC clone without the need for additional sub-cloning.

Our strategy has been to initially use these GT clones to screen cDNA libraries and to screen DNA and RNA from many HD patients in an effort to further refine the assessment of candidate genes. In this light, GT 24 which detects a large transcript clone close to an Alu retrotransposition event deserved further investigation. GT clones showing multiple bands on southern blot hybridization with excellent coding potential also warranted further consideration. For example, the transcription unit detected by GT 70 which has excellent coding potential, detects several genomic fragments, sees two distinct RNA species and also detects DNA changes or rearrangements in patients with HD.

GT 149 also detects transcriptional units and which also has excellent coding potention. The two transcriptional units are the same as those detected by GT 70. The two distinct mRNA species have respectively molecular weights of 10.3 kb and 13.7 kb. Such identified forms of the mRNA are due to variations in the 340 untranslated region of the HD gene. It is believed that the larger transcript which is present in the human brain in significantly increased mounts and as derived from the HD gene including the UTR HD 14 is closely associated with Huntington's Disease. The 3' UTR of HD 14 provides a useful entity for detecting, analyzing and the prognosis of Huntington's Disease in humans due to the selective increased expression of this entity in the human brain.

A transcriptional map as described in more detail in the Examples and used to develop the strategy in locating GT 70, GT 149 and HD 14, is equally applicable to any other genomic region and will greatly assist in the search for any disease gene. Furthermore, by cloning the disease gene, the development of a detailed transcription map of a particular region allows further assessment of the possible regulatory inter-relationships between genes in that region. In addition, antisense RNA or DNA can be provided to bind specifically with the HD gene mRNA, thereby interrupting the precise molecular choreography which express the gene as a protein. The antisense material provides a very useful form of gene therapy to possibly arrest HD progression in the brain and other tissue (J. J. Toulme et al. Gene Vol. 72, No. 1, pg. 51–58, December 1988).

Currently, there is considerable interest in the role of 3' untranslated (UTR) sequences (Jackson (1993) *Human Molecular Genetics* 2:901:907, Sachs (1993) *Cell* 74:413–421), which may have diverse functions. The 3' UTR of eukaryotic mRNA contain signals for mRNA localisation, polyadenylation and translation initiation and regulation. In addition, it has been reported that the UTR sequences control growth and differentiation of myoblasts and in the case of myotonic dystrophy, harbour the mutations associated with the disease.

We believe, the larger (13.7 kb) transcript associated with HD gene, plays a critical role in the pathogenesis of the disease. This is the predominant transcript in brain, whereas the 10 kb transcript is more abundant in a variety of other tissues including heart, muscle, liver, lung and intestine (Lin et al. (1993) *Human Molecular Genetics* In press). Thus, it is conceivable that a mutation in the 3' UTR of the larger transcript causes the disease. The HD 14 sequence can serve as an important diagnostic tool. More importantly, however, we can use this sequence for therapeutic purposes by incorporating it into vectors designed for gene therapy and perhaps also directly injecting antisense constructs and other reagents derived from HD 14 to specific regions of the brain. These techniques are already established and replication defective adenovirus vectors and herpes simplex virus based vectors are already being tested for gene therapy for other diseases (Breakefield (1993) *Nature Genetics* 3:187–189). Transgenic mice can incorporate the HD 14 sequence but with the expression profile of the 13.7 kb transcript altered by, for example, over-expression or even complete ablation in a tissue specific and a developmentally regulated manner. These approaches provide considerable potential for treatment of HD.

The following procedures and methods demonstrate various aspects to which the invention is directed and are to be interpreted in a manner to support the principles of the invention as they are set out in the scope of the appended claims.

EXAMPLE 1

MATERIAL AND METHODS

Cosmid Libraries

A flow sorted chromosome 4 cosmid library (Cell source: UV 20 HL21–27, hamster human hybrid cell lines containing human chromosomes 4,8 and 21) was kindly provided by Los Alamos, National Laboratory. This library is cloned in the vector sCos1 and is propagated in the *E. coli* host strain HB101. A human placental genomic cosmid library which utilizes the pWE15 vector and host strain *E. coli* AG1 (Stratagene) was also used.

Cosmid DNA Preparation and Probe Isolation

Cosmid DNA was prepared by the alkaline lysis method described by Birnboim and Doly. Probes used for chromosomal walking were prepared by electroelution from agarose gels or by isolation of low melting point agarose slices containing the insert DNA. $^{32}p$ labelled probes were prepared by random hexamer priming and routinely preannealed with 300 µg of sonicated total human placental DNA in TE, pH 7.5 at 65° C. for 1 to 6 hours prior to hybridization.

cDNA Preparation for Gene Tracking

Fetal brain mRNA was purchased from Clonetech Labs Inc. For total RNA preparations, tissue was disrupted by a Polytron homogenizer in guanidinium isothiocyanate and RNA was isolated by centrifugation through a CsCl cushion.

Total RNAs from bone marrow, adult liver and frontal cortex as well as poly $A^+$ RNA from fetal brain were reverse transcribed with M-MLV reverse transcriptase (Bethesda Research Labs) as recommended except that the oligonucloetide used for the priming had the sequence 5'CGGAATTCTCGAGATCT(N)$_5$A3'. First strand cDNA was separated from the primer by passage over an agarose bead column (A.5 medium, BioRad Labs) as described previously and the collected cDNA was tailed with dATP using terminal transferase (Bethesda Research Labs).

Second strand cDNA was then prepared by two rounds of extension with Taq polymerase using the oligonucleotide 5'CGGAATTCTCGAGATCT$_{(12)}$3'. The entire cDNA mixture was then expanded by 15 cycles of PCR with a single oligonucleotide with the sequence 5'CGGAATTCTCGAGATCT. The oligonucleotide corresponds to the beginning of both the first and second strands of cDNA. The position of the EcoRI recognition sequence used for cloning is underlined.

Transcribed Sequence Selection by Gene Tracking

Cosmids isolated at the D4S95 locus were transferred by blotting and immobilized onto nylon membranes (Hybond N$_+$, Amersham) by cross-linking. Two sets of membranes were then hybridized (as directed below) for two rounds, each for three day durations. cDNA was used that had been prepared from total frontal cortex RNA only, and for a second set, a pool of end specific cDNAs was prepared from poly A⁺ RNA of fetal brain (clonetech), and total RNA of bone marrow, liver and frontal cortex. The cDNAs were combined with 20 mass equivalents of sonicated human placental DNA. The mixtures were neutralized, pre-annealed for 60 minutes at 55° C. and diluted to a concentration of 10 μg cDNA/ml with Church hybridization solution and used for the first round of hybridization. Membranes were washed to a final stringency achieved with 0.2×SSC, C.05% SDS at 60 ° C. Bound cDNAs were then eluted by heating membranes in distilled water for 10 min at: 95° C. The eluted cDNAs were added to 10 μg of sonicated human placental DNA and precipitated. The precipitate was resuspended, denatured, pre-annealed and hybridized again to the immobilized cosmid clones.

Following the second hybridization, the membranes were washed and cDNAs were eluted. The collected material was passed over a G50 Fine Sephadex (Pharmacia) column and aliquots were subjected to amplification by PCR with the oligonucleotide that was initially used to expand the prepared cDNA pool. Following digestion with EcoRI restriction enzyme and separation on a 1.2% agarose gel, products greater than 0.4 kbases in size were isolated by Geneclean (BioCan Sci.). These products were cloned into pBluescript (Stratagene) that had been linearized with EcoRI restriction enzyme and treated with Calf intestinal phosphatase (Boehringer Mannheim).

Northern Blot Analysis

RNA was isolated using the single step method of homogenization in guanidinium isothiocyanate and fractionated on a 1% agarose gel containing 0.6M formaldehyde. The structural integrity of the fractionated RNA was confirmed by the presence of intact 28S (4.7 Kb) and 18S (1.8 Kb) RNA bands. The RNA was transferred to a Hybond N⁺ membrane (Amersham) and crosslinked with ultraviolet radiation. Ultraviolet cross-linking was done to ensure fixation of RNA to the membrane. Hybridization of the Northern blot with β-actin as an internal control probe provided confirmation that the RNA was intact and had transferred. Hybridization with cDNA was carried out in Church buffer (0.5M sodium phosphate buffer, pH 7.2.7% sodium dodecyl sulphate, 1 mM EDTA) at 58° C. overnight. Following hybridization, Northern blots were washed in 0.5×SSC, 0.1% SDS at 58° C. for 40 minutes followed by 10 minutes at 0.15×SSC, 0.1% SDS. Autoradiography was carried out for 1 to 3 days using Kodak XAR5 X-ray film at −70° C.

Southern Blotting

Human genomic DNA was isolated using standard method. DNAs were digested with 3 enzymes, MspI, PstI and HindIII according to the manufacturer's recommendation and after electrophoresis, transferred to Hybond N⁺ membranes (Amersham). All hybridizations were carried out in Church buffer at 65° C. overnight and washed with 0.5 ×SSC, 0.1% SDS at 650° C. Autoradiography was carried out for 1 to 7 days at 70° C.

Direct Sequencing of PCR Products

Asymmetric PCR was used to generate single strand DNA templates from PCR products as described in Sambrook et al. In brief, double strand PCR product was obtained after initial amplification of first strand cDNA. The PCR fragments were purified using Geneclean and used as a template for generating single strand PCR products using a 100:1 ratio of the 2 oligonucleotide primers for 45 cycles. When multiple PCR products were seen, specific bands were first excised from a low melting point agarose prior to Geneclean purification. Single strand asymmetric PCR products were purified by centrifugal filtration (30 000NMWL filter, Millipore) and finally sequenced using 1 pmole of the limiting primer by the dideoxy sequencing method (Sequenase Kit USB).

cDNA Library Screening

Fetal brain and frontal cortex libraries (Stratagene) were screened with cD506. Approximately 1 million plaque forming units were plated onto four, 24×24 cm² bioassay dishes (Nunc) and 2 sets of replica filters were made using Hybond N⁺ nylon filters (Amersham). The cDNA fragment (cD506) identified using the hybrid selection procedure was radiolabeled by the random priming method of Feinberg and Vogelstein. Prehybridization and hybridization were done in Church's buffer. Following overnight hybridization the cDNA filters were washed in 0.1×SSC, 0.1% SDS at 65° C. Autoradiography was carried out for 24–72 hours at −70° C.

Computer Assessment of DNA Sequence

Sequence was entered into a Sun Sparc IPC workstation using a sonic digitizer, and gel readings were assembled using the program Xdap. Sequences were sent to the National Centre for Biotechnology Information BLAST server to search for homology to known sequence. The PROSITE database was used to screen the adducin amino acid sequence for protein motifs.

RESULTS

Establishment of a Contig Around D4S95

A cosmid walk was initiated by screening a human chromosome 4 cosmid library with D4S95. Cosmids were obtained, digested in single and double digests and mapped to establish overlapping restriction fragments. To expand the cloned region, the T3 and T7 EcoRI end fragments of cosmid B1H1 were isolated and used to screen the same colony filters through two subsequent rounds of hybridization. The additional positive colonies were isolated, digested with restriction enzymes, and hybridized with the T3 or T7 EcoRI end fragments of cosmids of previous screenings to confirm that they extended the cloned region. A contig of approximately 85 Kb around D4 S95 was established (FIG. 1A).

Identification of Transcribed Sequences in the D4S95 Cosmid Contig

To determine if transcribed sequences were present in the cosmids originating from the D4S95 locus, a direct selection procedure with cDNA was applied. The scheme, which we term "gene tracking", is similar to that initially proposed by others with modification of the conditions for hybridization and employment of prepared cDNA sources that were not passaged through E. Coli. We have found this to provide the best source for transcribed sequences. In brief, cDNAs that had been generated to have sequence specific ends were hybridized to the cosmids from the D 4S95 contig which were mobilized onto nylon membranes. Then, following washing at high stringency, cDNA segments that had specifically hybridized were eluted, amplified by the polymerase chain reaction and cloned.

cDNA prepared from frontal cortex RNA as well as a pool of cDNAs that had been prepared from fetal brain, frontal cortex, bone marrow and liver RNAs were used as sources of transcribed sequences for the selection. Following the amplification of the material retrieved by hybridization to the immobilized cosmids, the products (0.2 to 1.5 kb) were ligated and used to transform E. Coli DH5 cells.

Plasmid DNA prepared from twenty-four individual clones (12 from each cDNA source) revealed insert sizes of 0.2 to 0.9 kb. Radio-labelled probes were prepared from six of the inserts and hybridized to blots of EcoRI digestions of the overlapping cosmids and mammalian DNAs. All six detected EcoRI fragments from the overlapping cosmids that corresponded in size to discrete human genomic DNA bands. It could be deduced that these clones with the retrieved transcribed sequences detected overlapping portions of a gene or genes with multiple exons. Most also detected cross-hybridizing bands in bovine and murine DNA. Analysis of the sequence of these clones indicated that they were portions of a previously identified germ, namely erythrocyte adducin (Table 1). Hybridization of cD506 to a series of cosmids confirmed that the cDNA identified was derived from the D4S95 cosmid contig (FIG. 1B).

Search for DNA Rearrangements

In an effort to identify a full length cDNA clone, the cDNA fragment cD506, from the 3' untranslated region (2995–3912) which was identified using the hybrid selection procedure was used to screen a frontal cortex and a fetal brain cDNA library. A 2.7 kb cDNA was identified from the frontal cortex library which was sequenced from both ends and found to have sequence corresponding to that for the α-adducin gene. This 2.7 kb cDNA which includes nucleotides 400–3080 of the erythrocyte adducin sequence, together with the 1.2 kb PCR fragment (ADU133–1357) were used to screen Southern blots of DNA from 100 affected HD patients digested with three enzymes (MspI, PstI, HindIII) in an effort to look for major rearrangements in the adducin gene. No major rearrangements in this gene were observed in 100 unrelated patients with HD.

A stretch of four AAG repeats followed 21 nucleotides later with another stretch of five AAG repeats was seen in the 3' end of the coding region of the gene of the control and 2 HD patients. The possibility of trinucleotide expansion was assessed by PCR using primers (ADU2162–2383) which flank these AAG repeats. Using polyacrylamide gel electrophoresis and Southern blot analysis, no difference in size was detected amongst the members of two HD families known to show strong anticipation (data not shown).

Northern Blot Analysis

Northern Blot analysis revealed a single transcript of approximately 4 kb in frontal and parietal cortex as well as basal ganglia of both control and HD patients. No alteration of the transcript was seen in lymphoblast RNA of a patient homozygous for HD (FIG. 2). The transcript was found to be widely expressed in multiple tissues including lymphocytes, bone marrow, liver, and an intestinal cell line (CaCO2).

Assessment of the Adducin Gene in 2 HD Patients and a Control

Oligonucleotide primer pairs spanning the coding sequence and the 5' and 3' untranslated regions were designed based on the published erythrocyte α-adducin sequence to generate PCR products ranging in size from 200–1200 bp. The condition for the PCR reactions and oligonucleotide primers that were utilized are shown in Table 2. Template cDNA was produced from RNA by reverse transcription. RNA was extracted from frontal cortex of 1 control patient and 2 HD patients (HD15 and HD40) with a confirmed family history of HD.

We have sequenced the entire coding region from each of 2 HD patients (HD15 and HD40) and one normal control (2210 bp). In addition, we have compared the 3' untranslated region between HD15 and control (1483 bp). Only a single sequence difference from the reported erythrocyte α-adducin gene was detected but occurred in both HD patients and the control samples. This sequence alteration was a G→G change at nucleotide position 1911 which predicts a serine instead of cysteine. Furthermore, we were unable to generate any PCR products upstream of nucleotide 133 which may reflect additional sequence differences in the 5' untranslated region of the brain α-adducin gene compared to the published erythrocyte sequence.

SSCP analysis of coding regions of the same 2 HD patients and control using 6% acrylamide and 10% glycerol gels revealed no band shifts, consistent with the results of sequence analysis.

Alternate Splicing of the Adducin Gene

Figure 3B:
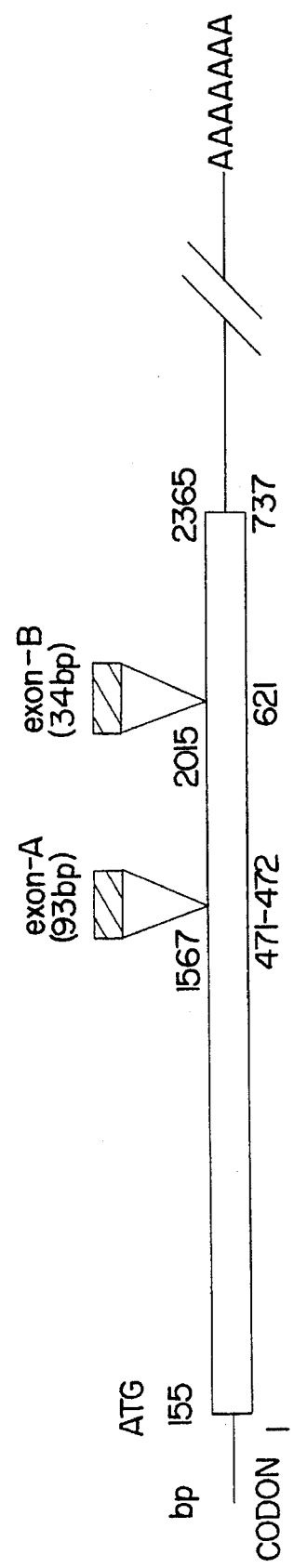

An additional band larger than the predicted size was detected on a 1.2% agarose gel after PCR amplification of cDNA using three different primer sets (FIG. 3). The larger bands from PCR products ADU1111–1615 and ADU1524–2005 were purified and directly sequenced revealing an alternately spliced exon of 93 bp (exon-A). Similarly, PCR product ADU 1912–2456 showed a doublet consisting of two bands of almost equal mobility on a 2% agarose gel. Sequencing of the 2.7 kb cDNA clone isolated from brain using primer ADU1912 identified an additional alternately spliced exon in brain of 34 bp (exon-B). Brain exon-A was sequenced in the control and 2 HD patients and no differences in sequence were detected.

The two alternately spliced exons not present in the erythrocyte cDNA were also found in the cDNA from the frontal and temporal cortex as well as basal ganglia of the control and both affected patients. Alternate splicing was also detected in temporal cortex and basal ganglia by PCR of cDNA libraries.

Exon-A introduces 31 amino acids between codon 471 and 472 without disrupting the reading frame. In contrast, exon-B interrupts codon 621 and introduces 11 amino acids before terminating in a stop codon. This shortened adducin protein lacks the functionally important carboxy terminus which contains a potential protein kinase C phosphorylation site and a calmodulin binding site.

EXAMPLE 2

Using a transcription map derived from the defined region we also obtained candidate genes for HD. To construct the map, three overlapping YACS were used which spanned the entire region of interest extending approximately 0.5 Mb proximal and distal from the D4S95 locus, the marker which most consistently shows non-random allelic association with HD. A total of 50 cDNA clones were isolated using direct cDNA selection. A total of 250 HD patients were screened with a series of cDNA clones (GT), one of which (GT 48) revealed an insertion of an Alu repetitive element in two families with identical DNA marker haplotypes on their HD chromosomes. In addition to complete segregation with HD in these two families, the insertion is not seen in 1000 control chromosomes in the general population. This includes 14/687 persons with an identical core haplotype suggesting a causal relationship between this rearrangement and HD. The insertion site is immediately adjacent to two overlapping transcriptional units including α-adducin and another which encodes for a 12 kb transcript.

Refinement of the proximal border of the candidate region for HD

The distal boundary of this region is defined by a crossover occurring between D4S98 and D4S43 and the proximal boundary by recombination between D4S10 and D4S125 (FIG. 4). In additional studies, nonrandom allelic association detected by D4S95 further refined the possible location of the HD gene. Assessment of other recombination events in affected families and further studies of allelic association has led to the designation of a second candidate region distal to D4S111.

Figure 5:
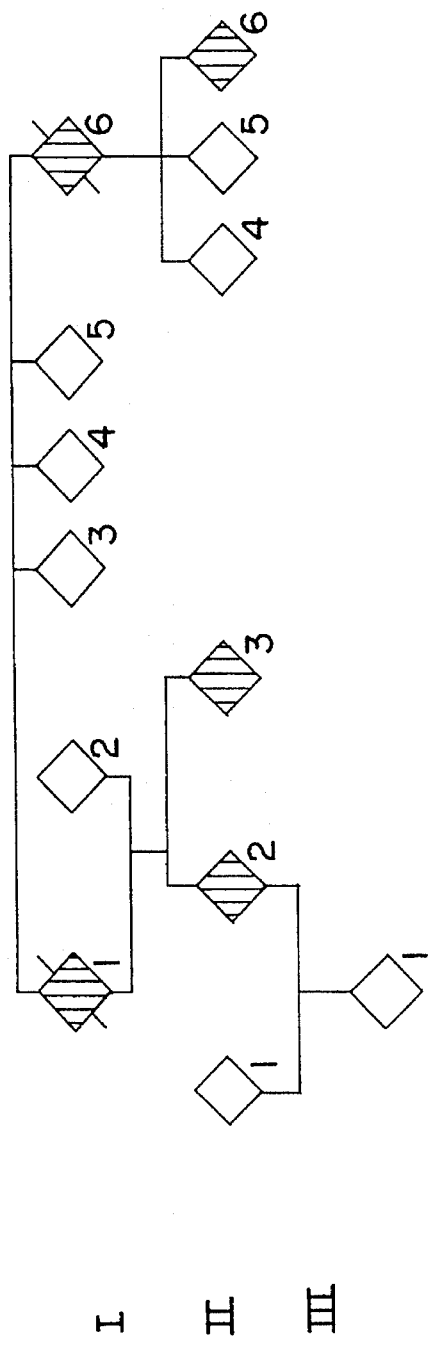

We have analyzed 250 HD families for recombination events between different markers in order to more precisely define the minimal candidate region likely to contain the HD gene. In only one family, a recombination event distal to D4S125 has been identified (FIG. 5). In this family with clearly documented HD in numerous individuals, the recombination event in individual II-6 implies that the mutation causing HD is distal to marker D4S125 thus reducing the candidate region for the HD mutation by at least 200 kb (FIG. 4 and FIG. 5).

Development of a transcription map

In the absence of any knowledge concerning the primary defect underlying HD, different strategies including delineation of CpG islands, cDNA isolation and exon amplification have been used to identify genes from both candidate regions.

To identify genes located in HD candidate regions, we have used a direct cDNA selection strategy on three overlapping YACS which span the region of interest with minimal overlap. Purified YACs immobilized on filters were incubated with single or combinations of primary cDNA pools made from 4 different tissues including fetal brain, frontal cortex, liver and bone marrow. Following two rounds of hybridization, libraries of selected cDNAs were prepared, arrayed and screened for presence of repetitive sequences as described previously.

The origin of the clones was confirmed by hybridization to EcoRI-digested DNA from human, human-hamster hybrid containing only human chromosome 4 and the original YAC clones. Each clone was also mapped to a panel of DNAs of overlapping YACS with one or more restriction enzymes to sub-localize their position into 5 "bins" (BIN 1-5) as depicted in FIG. 4.

Figure 6:
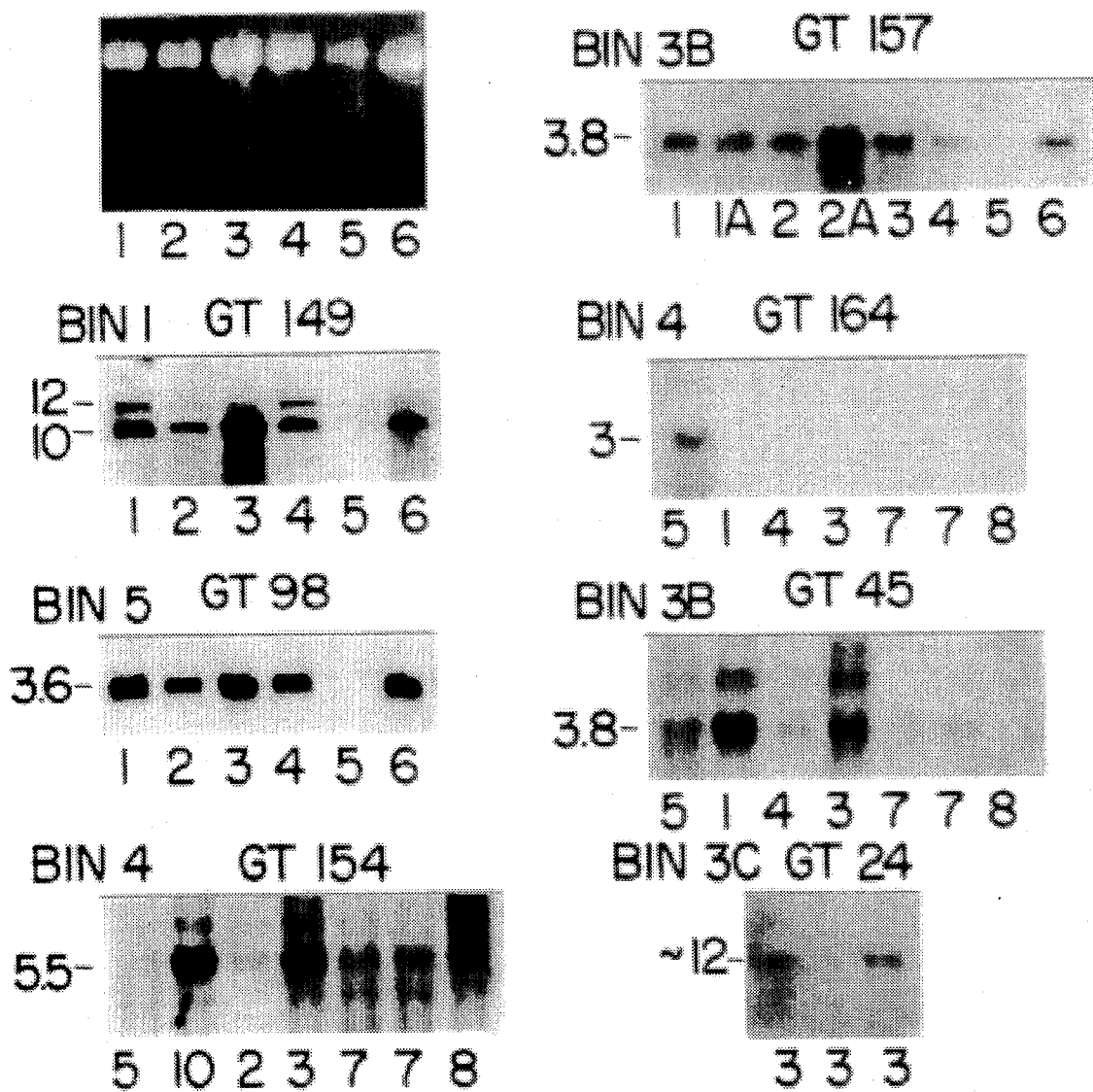

In addition to refined physical mapping, the clones were also categorized into transcription units by cross-hybridization to each other and to RNA from a variety of tissues and cell lines. The results for seven GT clones are shown in FIG. 6 of the clones that were isolated from the 70D11 YAC, one group was found to correspond to the α-adducin message previously identified[12].

The remaining clones were subjected to direct sequence analysis which revealed that several of the clones contain open reading frames but that there were also clones for which open reading frames could not be detected. In total, at least 7 transcription units with different transcript sizes could be defined by the cDNA clones in the tissues tested. Further physical mapping of these clones identified a subset of clones which mapped to the proximal candidate region between D4S127 and D4S182 which contains D 4S95 and also encompasses DNA markers which form the core haplotype that is present on about one third of disease chromosomes[18].

Detection of Rearrangements in HD Families

By using additional overlapping YACS we were able to subdivide BIN 3 which contains D4S127, D4S95, and D4S 182 into 3 compartments, BIN 3A, 3B and 3C (FIG. 4). A total of 16 cDNA clones mapped to BIN 3 of which six have previously been shown to encode the α-adducin gene[13]. The other 9 were grouped based on their hybridization to different YACS (FIG. 4) and to a cosmid-phage contig from this region as well long range mapping by pulsed field electrophoresis (Lin et al. in preparation).

We have screened for rearrangements with those GT clones that map to BIN 3. One GT clone, GT 48 detects an insertion of approximately 330 bp in 2 of 250 HD patients. This rearrangement segregated with HD in both families (FIG. 7a, 7b) and was seen in genomic DNA digested with multiple enzymes (FIG. 7c). Interestingly, in one of these families (FIG. 7A) recombination had placed the HD gene distal to D4S125 (FIG. 5).

The rearrangement was not seen in 1,000 control chromosomes. The fact that this rearrangement occurred on the same haplotype in both families and that this haplotype was unique among 140 HD families further suggested a common origin for this rearrangement (FIG. 5). Both families were of Scottish origin with their ancestors living 50 km apart. The core chromosomal haplotype extending for about 1 Mb including alleles at D4 S95 and D4S98 is seen in 2% (14/687 chromosomes) of the general population. Normal individuals with chromosomes with this core haplotype do not have this arrangement.

Alu Retrotransposition

Detailed restriction mapping localized this rearrangement to a 1.2 kb HindIII fragment which contained a portion of GT 48 (FIG. 8 a). Sequence analysis of the rearrangement in both families demonstrated an insertion element of 331 base pairs which is a member of the Alu family of mobile repetitive elements. With primers flanking the insertion site, the inserted element could be detected using PCR (FIG. 8b).

Only a few Alu elements have been described which are transcriptionally active in vivo of which the HS Alu subfamily represents the most recently inserted group[19-20]. DNA sequence analysis of this Alu rearrangement (FIG. 8a) shows an insertion by retrotransposition as the Alu element is flanked by a perfect 9 base pair duplication of the target sequence, characteristic of insertions of mobile elements into staggered single stranded nicks at different genomic locations. Furthermore, the sequence corresponding to the insertion is AT rich which is consistent with the hypothesis that Alu elements preferentially integrate into AT rich regions[21] (FIG. 8a).

Detection of Candidate Genes for HD Near the Alu Insertion Site

As previously described, several GT clones allowed the identification of cDNA for the α-adducin gene[12]. The 3' UTR of α-adducin maps 20 kb telomeric to D4S95[12] (FIG.

Figure 9:
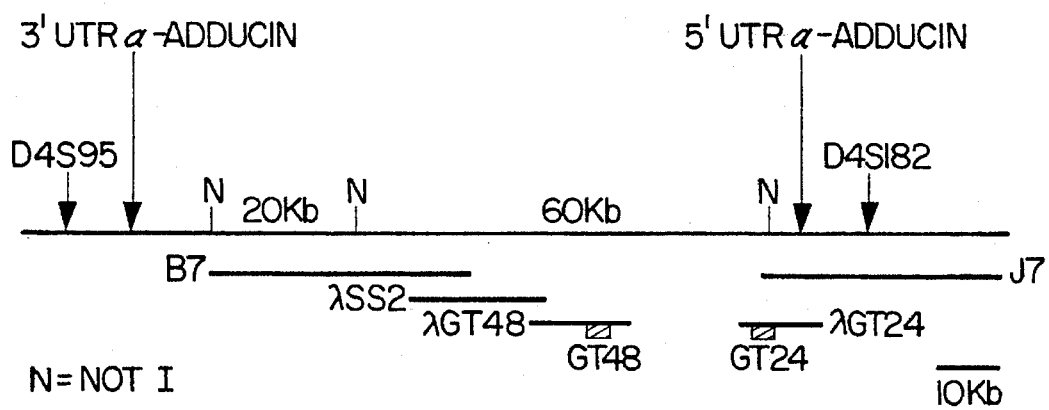

9). An oligonucleotide primer which spans nucleotide 38–58 in the 5' untranslated region of the α-adducin gene maps telomeric to the Alu insertion and is located on the same 7.4 kb EcoRI fragment as GT 24 but does not hybridize to GT 24 (FIG. 9). In addition, a 501 bp RT-PCR product corresponding to nucleotides 38–539 of the α-adducin cDNA also detected the 7.4 kb EcoRI fragment. This places the 5' UTR of the α-adducin gene in close proximity to D4S182, flanking GT 24 and indicates that the α-adducin gene spans at least 80 kb between D4S 95 and D4S182 (FIG. 9).

Since the sequence spanning the Alu insertion showed no identity with the coding region of α-adducin, the insertion has occurred within an intron, near the 5' end of the α-adducin gene. No quantitative or size alterations in the α-adducin gene have previously been detected in RNA prepared from HD heterozygotes and potential homozygote for HD[12]. Further, no sequence alteration could be detected in the α-adducin cDNA from 2 unrelated HD patients[12]. Therefore, it is unlikely that the Alu insertion affects the expression of α-adducin gene but this possibility has not been totally excluded.

Corresponding transcript(s) for GT 48 and the two other adjacent clones, GT 44 and GT 49, were not detected. Northern blot analysis and screening of 10 different cDNA libraries with these cDNA clones did not yield any positive results. Sequence analysis of the 1.2 kb HindIII fragment containing GT 48 did not reveal a significant coding potential.

Nevertheless, the presence of a new Alu element might interfere with expression of other genes near the site of insertion. We therefore focused our attention on two other cDNA clones. GT 24 and GT 34. Northern blot analysis showed that GT 34 detected a 4 kb transcript in a variety of tissues including brain, lymphoblasts and fibroblasts. A 4 kb cDNA clone (cD 510) was then isolated with GT 34 as probe. Sequence analysis of this cDNA clone revealed no homology with sequences in Genbank. Further mapping data showed that the genomic DNA sequence corresponding to cD510 mapped distal to D4S95, but centromeric to the 3' UTR of α-adducin and at least 70 kb from the site of the Alu insertion (FIG. 4). Based on the map location, therefore, cD510 became an unlikely candidate for the HD gene.

The third clone, GT 24, was mapped approximately 20 kb from GT 48 (FIG. 9). Although GT 24 is also contained in an intron of the α-adducin gene it detected a different transcript of 12 kb (FIG. 4, FIG. 6) in many tissues including frontal cortex, fibroblasts, lymphoblasts, and intestinal cells (CaCO2). Besides some weak identity with the LINE-1 element, this clone also has no homology with any sequence in the data bases. However, at 69 bp open reading frame flanked by appropriate splice junctions was noted [23]. Furthermore, based on its map position close to the Alu insertion site, the 12 kb transcript is a candidate gene for HD.

EXAMPLE 3

MATERIALS AND METHODS

Growth and Isolation of YAC DNA

Yeast cultures (50 ml) were propagated and grown as described. Concentrated chromosomal preparations were prepared by scaling as described. The individual chromosomes were separated with the CHEF-DR-II Pulsed Field Electrophoresis System (Bio-Rad Labs) using standard conditions. No effort was made to eliminate the co-migrating yeast chromosome with each YAC. The chromosome containing human DNA was sliced out, stained in diluted loading dye and embedded in near solidified agarose. Upon solidification, the gel was treated and transferred to membrane as described previously. The DNA was immobilized onto the membrane by UV cross-linking which was then trimmed to include only the portion containing the YAC DNA.

cDNA Preparation cDNA was prepared from poly A$^+$ RNA (fetal brain) or total RNA (frontal cortex, liver, and bone marrow) as described previously. Briefly, RNAs were reverse transcribed by random priming using an oligonucleotide (5'CGGAATTCTCGAGATCT(N)$_5$A). The first strand cDNA was then tailed with terminal transferase in order to generate the second strand using a second primer (5'CGGAATTCTCGAGATCT$_{(12)}$). These incorporated end sequences permitted expansion of the cDNA, by PCR amplification and facilitated the cloning of the selected cDNAs by the use of a single primer 5'CGGAATTCTCGAGATCT for all tissue sources.

Transcribed Sequence Selection

Membranes with the mobilized YAC DNA (200–400 ng) were hybridized for two rounds each for three day durations at 60 ° C. in Church hybridization solution as previously described. Prior to the first and second hybridizations, the cDNA pools were pro-annealed with human placental DNA. 10 µg of cDNA was used per ml of hybridization solution for the first round. Washings were carried out with 0.2×SSC and 0.05% SDS at 60° C. The eluted material was passed over a G50 Fine Sephadex (Pharmacia) spin column and used directly for amplification. Amplified material was concentrated and digested with EcoRI restriction enzyme. The products were separated on a 1.4% agarose gel and fragments larger than 0.4 kb were isolated with glassmilk (GeneClean, BioCan Sci.) and finally cloned into the EcoRI site pBluescript (Stratagene).

The selection procedure was carried out with cDNA from frontal cortex RNA only (for 353G6, 70D11 and 2A11 YACs) from fetal brain RNA only (70D11 and 2A11 YACs) and from a pool of cDNAs (tissue mix) prepared from fetal brain, frontal cortex, bone marrow and liver RNA (for 353G6, 70D11 and 2A11). The membranes with the immobilized YACs were hybridized together but elution, amplification and cloning steps were carried out separately for each YAC.

Characterization of Retrieved cDNAs 100 individual transformants from each ligation were picked and arrayed onto an ampicillin plate for ordering, pre-screening and storage. Grown colonies were transferred onto Biotrans membrane (ICN) and denatured, neutralized and baked in a vacuum oven. The membrane was then screened with randomly primed total cDNA to determine which clones contained repetitive sequence. Plasmids from 20 to 40 clones from each selection experiment that had not hybridized in the pre-screen were then isolated and characterized. The human-hamster hybrid containing chromosome 4 (GM10115) was obtained from NIGMS Human Genetic Mutant Cell Repository, Camden, N.J.). Yeast and mammalian DNAs were prepared as previously described. Restriction digestions were carried out according to suppliers recommendations and electrophoresis and blotting to Hybond membrane (Amersham) was carried out according to standard procedures.

Of the cDNA clones selected from frontal cortex cDNA and from the tissue mix cDNA pool, 6/11 and 10/12 clones respectively mapped appropriately to the 353G6 YAC. A total of five of these also mapped to the region that overlapped with the 70D11 YAC. Of the cDNAs selected with frontal cortex cDNA and the tissue mix pool, 19/24 and 1/2 clones respectively mapped appropriately to the 70D11 YAC. Overall less material was retrieved from the 2A11 YAC suggesting that fewer transcribed sequences are present in this region. Of a total of 30 clones tested from the tissue mix cDNA pool, 15 originated from the YAC. Additional clones were also obtained from the 70D11 and 2A11 YACs by selection with fetal brain cDNA that had been prepared from poly $A^+$ RNA. Lower numbers of clones from this source (20%) which did not map back. While the number and nature of genes present in the genomic DNA would influence the outcome, it appeared that the inclusion of cDNA prepared from total RNA yields higher proportions of clones that mapped correctly.

RNA Preparation and Hybridization Analysis

Tissue was disrupted by a Polytron homogenizer guanidinium isothiocyanate and cells in tissue culture where suspended directly in guanidinium isothiocyanate. Total RNA was isolated by centrifugation through a CsCl cushion. For hybridization analysis, RNA was fractionated on agarose gels (1%) containing 0.6M formaldehyde and transferred to Hybond membrane (Amersham). Following cross-linking with UV radiation, blots were repeatedly hybridized with cDNA fragments radio-labelled by random priming. Final conditions for washing included 0.2×SSC with 0.1% SDS at 60° C. Blots were exposed to X-Omat AR (Kodak) film for 1–8 days with single intensifying screens at −70° C. Labelled probes were removed from membranes between hybridizations by heating to 95° C. with 0.02×SSC and 0.01% SDS.

Sequencing and Analysis

Manual or automated (ABI 373A) sequence data were obtained and entered into a Sun Microsystems Sparc IPX workstation and compared with previously entered sequence data (of GT clones) using the XDAP module of the Staden package. Sequence data were then sent to the e-mail server at the National Center for Biotechnology Information (NCBI) and compared with the non-redundant GenBank, dbEST, Macvector and Transcription Factor databases using the BLAST suite of programs. The CRM module of the Gene Recognition Analysis Internet Link (GRAIL) e-mail server was used to assess protein-coding potential and a search for open reading frames bracketed by splice junctions was conducted with the SORFIND program. The PYTHIA e-mail server was used to identify and classify known human repeat elements.

RESULTS

Strategy

Figure 10:
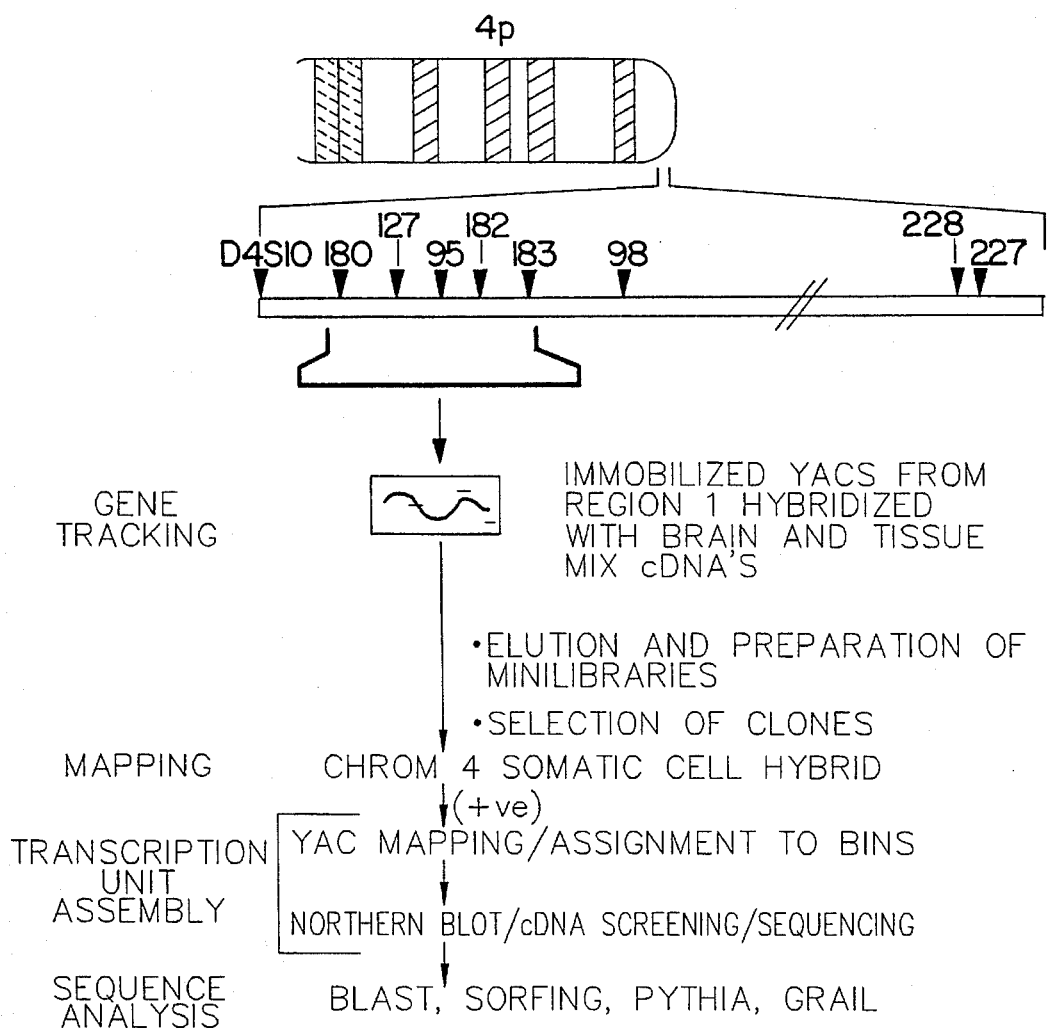

The overall strategy used to generate the transcription map is outlined in FIG. 10. Immobilized and purified YACs (353G6, 70D11 and 2A11) were subjected to two rounds of prolonged hybridization with cDNAs from frontal cortex or with pools of cDNAs from four tissue sources including fetal brain, frontal cortex, bone marrow and liver. Eluted cDNAs were then amplified by the polymerase chain reaction (PCR) and cloned to yield a library of selected cDNAs for each YAC. The clones of these libraries were arrayed and screened for presence of repetitive sequence, and the remaining clones (varying in number from 70–90%, depending on the starting YAC) were then individually hybridized to EcoRI digestions of human, human-hamster hybrid that contains human chromosome 4 and YAC clone DNAs in order to confirm their origin. These clones were then hybridized to each other to test uniqueness, hybridized to a series of additional overlapping YACs for physical mapping, hybridized to RNAs of tissue or cell lines and finally characterized by sequencing.

Physical Mapping

A high proportion (between 50%–90%) of clones were found by hybridization to originate from chromosome 4 and from the original chromosome 4 YAC (see Methods section). The structural integrity of the human DNA within the YAC was confirmed by the comparison of hybridization patterns observed for each clone to YAC DNA and to human and human-hamster hybrid DNAs. For these, the hybridizing EcoRI fragments of the YAC DNAs correspond to those observed with human total genomic and DNA of chromosome 4.

A series of additional overlapping YACs were also used to define physical intervals or BINs across the 1 megabase region as depicted in FIG. 11A. Refined positioning of each cDNA was deduced by the hybridization pattern to this array of YACs. For example, the hybridization pattern of clone GT70 (FIG. IIB) is consistent with it originating from the overlapping portions of the 353G6 and 70D11 YACs, in BIN 2. As well, this clone detected multiple bands indicating that it contains more than a single exon and also displayed striking cross species hybridization. The GT 48 clone (FIG. 11C) detected two HindIII restriction fragments in three of the YACs suggesting it originates from BIN 3B. It detected only a single EcoRI genomic fragment and did not show cross species hybridization. An additional 56 clones were mapped in a similar manner and the results are listed in Table 3.

Refined map position was obtained for two cDNA fragments which were located at the ends of the 70D11 YAC. The hybridization pattern seen with GT 70 on the different YACs (FIG. 11B) and chromosome 4 hybrid and human DNAs, (data not shown) indicate that this clone in all likelihood maps to the end of the human DNA segment in the 70D11 YAC and is entirely contained within the other YACs to which it hybridized including 33306. Through a similar analysis the clone GT 133 from BIN 4 was found to originate from the other end of the 70D11 YAC.

Mapping into Transcription Units

The clones were categorized into transcription units by hybridization to RNA from a variety of tissues including those initially used to select the cDNA fragments. The results are compiled in Table 3 and hybridization to RNA of Caco-2 cells, HL-60 cells, fibroblasts, lymphoblasts, or to frontal cortex brain tissue is shown for five clones in FIG. 12. Based on their expression pattern and size, a total of nine different mRNAs were detected.

The combined information of RNA hybridization and physical mapping clearly indicate that some of the GT clones were portions of the same transcription units. GT 70 and GT 149 (FIG. 12), for example, both detect the same distinct pair of very large transcripts (10 and 12 kilobases). Furthermore, GT 70 and GT 149 map close to each other (FIG. 11 and Table 3), but they do not cross-hybridize nor overlap by sequence analysis. Both GT 70 and GT 149 have excellent coding potential as judged by the GRAIL e-mail server (FIG. 13 and Table 3). Furthermore, GT 63 hybridized to EcoRI fragments that were identical in size to those detected by GT 70 and was found by cross-hybridization to overlap with it (Table 3).

Of the clones that were examined from the 70D11 YAC, five clones were found that corresponded to the previously identified and abundantly expressed α-adducin message. This was determined in a single cross-hybridization experiment with full length cDNA. As well, these retrieved cDNAs hybridized with EcoRI genomic fragments that corresponded in size to fragments expected from the genomic organization of this gene.

Overlapping clones were found by cross-hybridization of individual clones to all others or by sequence analysis. For example, GT 98 which detects a 3.6 Kb transcript hybridized to two other clones in BIN 5 (Table 3). One of these, GT 123, is also located in BIN 5 but only weakly cross-hybridized to GT 98 and does detect a transcript of identical size. That these clones overlap was also supported by examining the EcoRI genomic restriction fragments to which these clones hybridized (Table 3).

Sequencing indicated the majority of clones selected were independently derived. Some of the overlapping clones (Table 3) detected abundant mRNAs. An exception was noted for GT 23 of BIN 3 which was derived from frontal cortex cDNA, did not detect mRNA and yet showed overlap with five other clones of 100 examined. It also hybridized to clones originating from fetal brain cDNA from a different selection experiment. Cross hybridization did not occur from repetitive sequence, as all of these clones hybridized to a single EcoRI band in genomic DNAs. This does suggest a preferential selection of this sequence through the process of hybridization to the immobilized genomic DNA or during amplification of the retrieved material. This preference was not evident with the tissue mix cDNA selection as GT 23 detected only two clones (both of which were not characterized further) of 100 tested, indicating that selection with a wider diversity of starting cDNAs may minimize the preferential retrieval of some sequences.

In addition to the patterns of DNA and RNA hybridization, sequence analysis was performed to determine cDNA overlap, their coding potential and to search databases of sequenced genes for identity or similarity. Many clones appeared to have been derived from unprocessed RNA since they lacked consistent open reading frames. Potential or partial exons were detected in them using the SORFIND program. Out of 31 non-overlapping clones, 5 showed identity with α-adducin and one, GT 161, was identical with the expressed sequence tag HUMXT01095.

One cDNA fragment appeared to detect additional sequences. For example, GT 161 which showed identity to an expressed sequence tag, hybridized strongly to the 2A11 YAC DNA digested with EcoRI and to a band of corresponding size in total human DNA (Table 3). A less prominent hybridizing band was also observed in human DNA that corresponded in intensity and size to one seen in a human-hamster hybrid containing chromosome 1 as its only human material, suggesting this clone represents a portion of a gene which may belong to a gene family (Table 3).

EXAMPLE 4—Location and Sequences of UTR of HD 14

Screening of cDNA Libraries

About one million plaque-forming units of each library were plated onto six 24 by 25 $cm^2$ petri plates (BIBCO), and two sets of replica filters were made using Hybond $N^+$ nylon filters (Amersham) by standard methods. Radio-labeled probes were prepared by random hexamer priming. Filter prehybridization and hybridization were performed in 0.5M sodium phosphate buffer, pH 7.2, 7% sodium docecyl sulfate, and 1 mM EDTA at 65° C. Autoradiography was performed for 24–72 h. Following second and tertiary, screening, positive plaques were subcloned into plasmid vectors.

RNA Preparation and Hybridization Analysis

Tissues were disrupted by a Polytron homogenizer in guanidinium isothiocyanate. Cells in culture were washed with PBS and suspended directly in guanidinium isothiocyanate. Total RNA was then isolated by centrifugation through a CsCl cushion. Poly $A^+$ brain and fetal brain RNAs were purchased from Clonetech, Inc. Poly $A^+$ RNA from CaCO-2 was prepared using a Fast Track® mRNA kit (Invitrogen).

For hybridization analysis, RNA was fractionated on agarose gels (1%) containing 0.6M formaldehyde and transferred to Hybond membrane (Amersham) according to standard procedures.

Following cross-linking with UV radiation, blots were hybridized with cDNA fragments radio-labeled by random priming. Final conditions for washing included 0.2×SSC with 0.1% SDS at 60° C. Blots were exposed to X-Omat AR (Kodak) film for 1–10 days with single intensifying screens at −70° C. Labeled probes were removed from membranes between hybridization by washing blots (3×) in 0.02×SSC and 0.01% SDS at 95° C.

DNA Sequencing

Plasmid DNA was prepared using a Qiagen plasmid DNA preparation column. Automated sequencing was performed using the ABI 373A sequencer. Sequencing and PCR primers were synthesized with Applied Biosystems, Inc. PCR Mite 391 synthesizer.

Southern Blot Analysis

The human hamster hybrid containing chromosome 4 (GM 10115) was obtained from NIGMS (Human Genetic Mutant Cell Repository, Camden, N.J.). Cosmid DNAs were digested with restriction enzymes (BRL) according to the manufacturer's recommendations and after electrophoresis, transferred to Hybond $N^+$ membranes (Amersham). All hybridizations were carried out in Church buffer at 65° C. overnight and washed with 0.5 ×SSC, 0.1% SDS at 65 ° C. Autoradiography was carried out for 10 to 30 minutes.

PCR Analysis

PCR reactions were carried out using Promega PCR buffer and 1.5 mm $MgCl_2$. Amplification was performed for 30 cycles (45 sec it 95° C., 30 sec at 58° C. and 2 min at 72° C.).

DNA Sequence Analysis

Searches for homology to all published DNA and Protein sequences were carried out using the NCBI BLAST server, running on SUN sparcstations under SUNOS.

A combination of general purpose text processing software and local sequence analysis software was used to extract subsets of the large public data bases based on feature table entries for poly A sites and for 3' UTR regions. These subset data bases were searched using a complete dynamic programming algorithm.

Routine sequence analysis, such as translations, oligosequence searches and alignments was also done using locally generated software.

RNA folding was examined using dot matrix plot methods, and with the "mfold" program of Jaeger and Zuker.

The "pythia" server was used to determine whether the sequence contained well known repeat sequences.

Identification of cDNAs Corresponding to the HD Transcript

Figure 14:
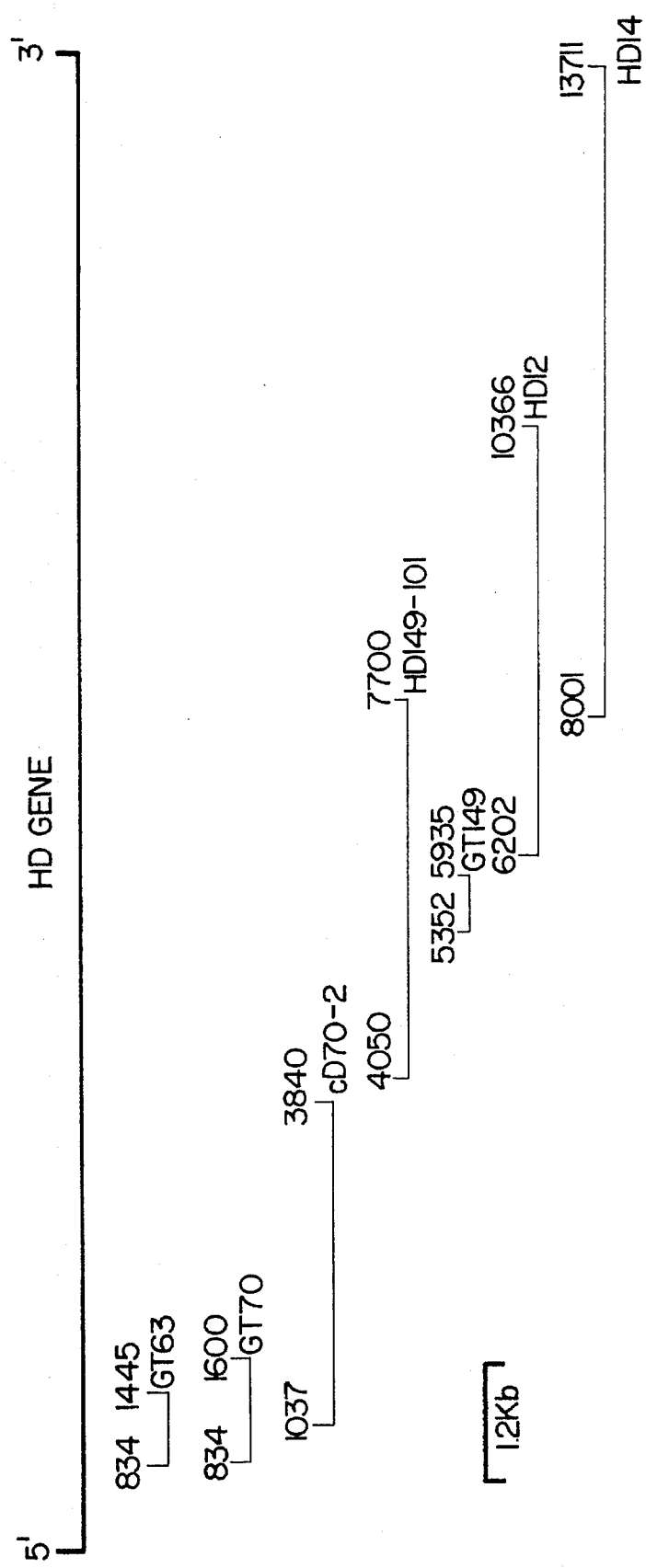

As part of our strategy to detect the transcriptional units originating from the region spanning 500 kb on either side of the D4 S95 locus, we previously isolated 58 cDNA segments. Three of the CDNA clones (GT 149, GT 63 and GT 70) (FIG. 14) were found to correspond to the sequence of the HD gene. Using two of these nonoverlapping cDNAs (GT 70 and GT 149), we screened a human frontal cortex cDNA library and identified two larger cDNA clones (cD 70-2 and HD 149-101) (FIG. 14). HD 149-101 and cD 70-2 were used to screen a number of other human cDNA libraries including those of retina, frontal cortex, fetal brain, caudate, and muscle tissues. In addition, a 1 kb PCR product corresponding to nucleotide 8000–9000 of the published sequence, was also used to screen the frontal cortex library. Additional cDNAs were identified including HD 12 and HD 14.

Sequence Analysis

All the CDNA clones were subjected to DNA sequencing and analysis. The sequence of HD 14 is deposited in Genbank (Accession Number L20431). HD 12 and HD 14 share identical protein coding sequences but differ in size and sequence of their 3' untranslated regions. HD 12 spans 4164 bp and its 3' end which has a putative untranslated sequence of 600 base pairs ends with a tall of 18 As similar to the published sequence. However, HD 14 which begins at nucleotide 8001 of the published sequence has 3,360 bp additional sequence distal to bp 10,350 (FIG. 14) and ends with a tail of 40 A residues (FIG. 15). HD 14 has a total of 3' UTR (untranslated region) of 3921 bp. In HD 14 two distinct putative polyadenylation sequences were detected including AGTAAA at position 10,326 and the hexanucleotide ATTAAA at position 13,645 of the HD 14 cDNA. The signal at position 10,306 corresponds to that in the previously published cDNA, and in HD 12. In addition, three other potential polyadenylation signals are seen in HD 14 including ATTAAA at position 11,109, AGTAAA at position 12,067 and CATAAA at position 12,095.

Genomic Organization of the 3' end of HD 14

Figure 16:
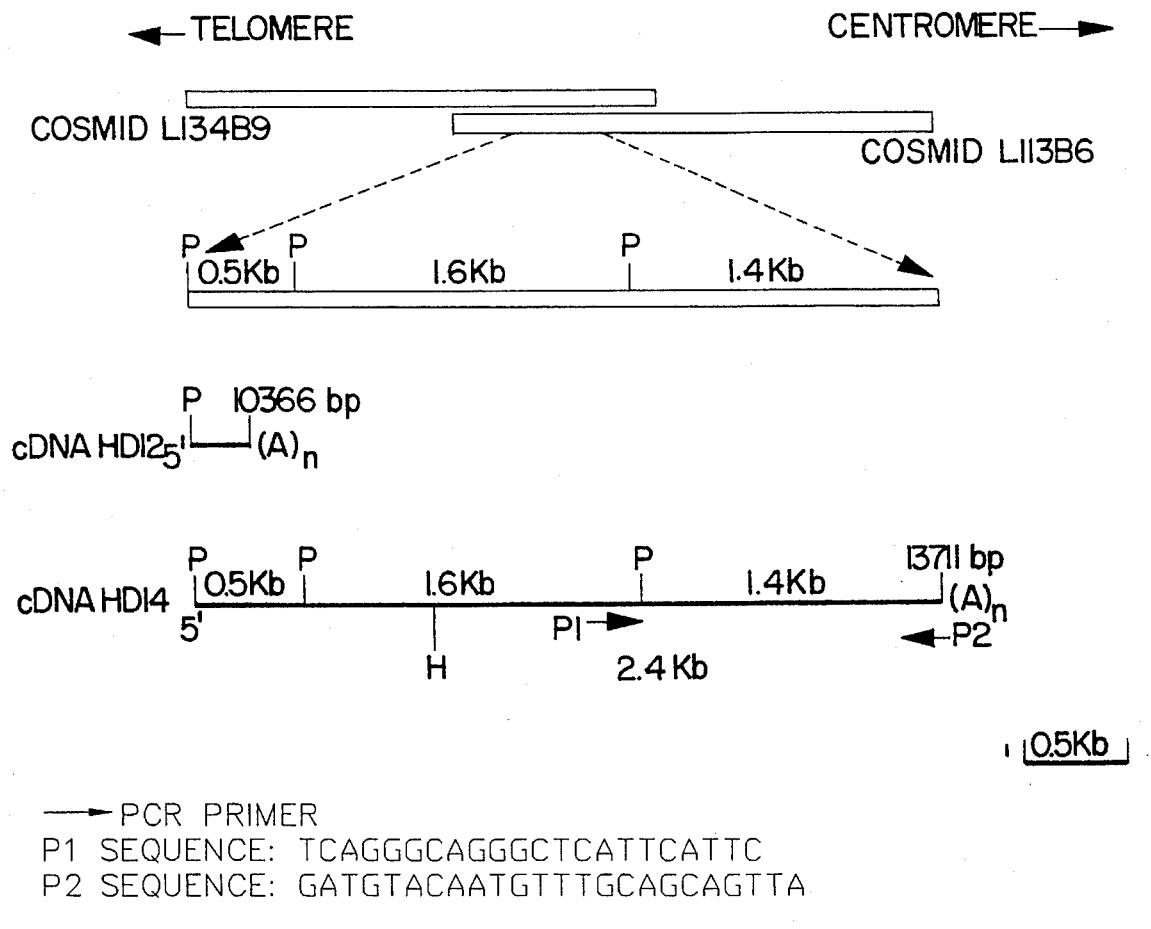

Two cosmids containing the 3' end of the HD transcript were selected from an arrayed chromosome 4 cosmid library provided by the Los Alamos National Library based on the notations in the published data. Both cDNA clones, HD 12 and HD 14 hybridized to both cosmids L 134B9 and L113B6. Restriction analysis of HD 14 identified unique fragments including, a 1–6 kb PstI fragment and a 2.4 kb HindIII fragment (FIG. 16). Hybridization of the 0.5 kb and 1.6 kb PstI fragments to cosmids L113B 6 and L134B9 as well as cDNA HD 14 identified DNA fragments of identical size. In addition, the unique 1.6 PstI fragment hybridized to an identical fragment from a YAC encompassing the 3' end of the gene. Furthermore, PCR analysis of both cosmids and cDNA HD 14 using primers flanking the unique 1.4 kb end fragment of HD 14 revealed the same sized fragment. This indicated that the 3360 bp non-overlapping cDNA fragment of the 3' UTR of HD 14 contains no additional exons but extends beyond the 3' end of the shorter clone.

Northern Blot Analysis

Figure 17:
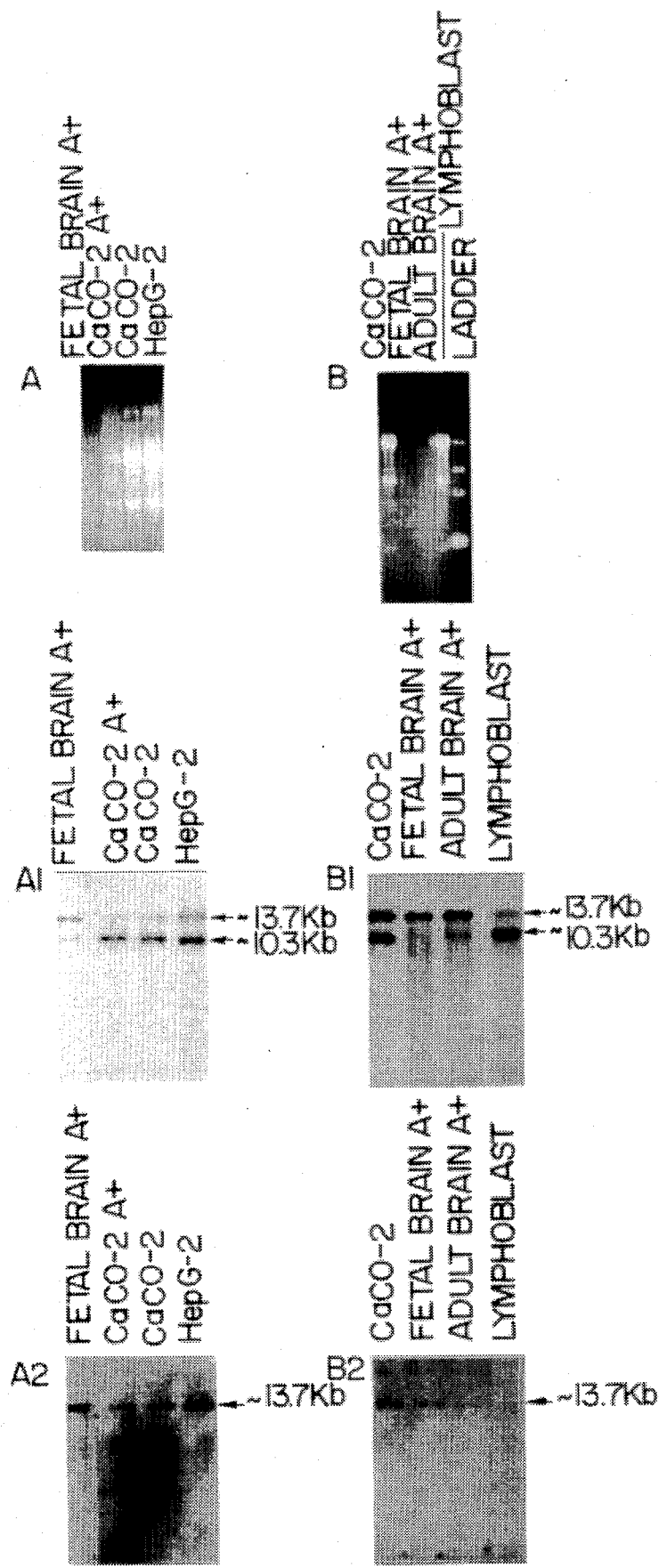

GT 70, GT 149 and cD 70-2 detected two mRNA transcripts in all tissues assessed including total and/or poly $A^+$ RNA from lymphoblast, frontal cortex (FIG. 17), intestine, liver and lung (data not shown). Similarly two transcripts were seen in total and poly $A^+$ RNA from a number of cell lines including lymphoblast, CaCO-2, Hep G2 (FIG. 17), HL 60 and 293S cells (data not shown) (FIG. 17). Using conditions that discriminated between human and rodent transcripts, these mRNAs were also both observed (data not shown) in the hybrid cell line GM 10115 containing chromosome 4 as its only human component indicating that both transcripts originate from chromosome 4. Furthermore all hybridizing genomic bands detected by these cDNA fragments could be accounted for between total human, chromosome 4 and YAC DNA (data not shown). This information provides further evidence that the two messages in all likelihood correspond to a single HD gene.

The larger mRNA is the predominant transcript in adult and fetal human brain compared to lymphoblasts and cell lines including Hep G2 and CaCO-2 where the smaller sized transcript is more abundant (FIG. 17). This was confirmed by densitometry analysis which showed a decreased intensity of approximately 3 fold in the ratio of the smaller to the larger transcript in adult and fetal brain. In contrast, in lymphoblast and cell lines as noted and in human intestines, liver and lung, the smaller to larger transcript ratio was increased in intensity by at least 2 fold. The non overlapping 2.4 kb HindIII and 1.4 PstI/EcoRI fragments of HD 14 were used in Northern Blot analysis and in contrast to the two transcripts detected with GT 70, GT 149 and cD 70- 2, only the single larger 13.7 kb mRNA was detected (FIG. 17).

The earlier finding that the GT 70 and GT 149 corresponding to the HD gene detected two different sized mRNA species (Experiment 3) prompted an investigation of the relationship between these two mRNA species. We uncovered partially overlapping but distinct cDNA clones which span 4164 bp (HD 12) and 5,710 bp (HD 14) respectively. The region of overlap between these two cDNAs and the HD sequence shows an identical protein coding sequence, but in HD 14 an additional 3,360 bp of non-coding sequence is identified.

This experiment demonstrates that the identified cDNAs (HD 12 and HD 14) originate from a single gene by DNA-hybridization analysis, restriction mapping and sequencing. Several mechanisms can lead to generation of different mRNAs from the same gene. Differential splicing events, alternate use of transcription start sites, or the selection of different polyadenylation sites can lead to multiple mRNA species generated from the same genomic region. Our experiments show that differential polyadenylation results in a larger transcript detected by RNA hybridization. It is generally appreciated that the majority of eukaryotic mRNAs possess a poly A tract at their 3' terminus. The addition of poly A occurs post-transcriptionally in the nucleus and involves cleavage of the primary transcript and subsequent addition of poly A to the newly formed 3' end. The cis-acting sequence usually AATAAA, located 15–25 nucleotides upstream of the poly A addition site, is highly conserved and critical for polyadenylation. Alterations within these cis-acting sequences can lead to the reduction or even abolition of 3' processing. Both the hexanucleotides seen in the HD 12 and HD 14 cDNAs have substitutions within this consensus that would be predicted to reduce the cleavage of the primary transcript and subsequent addition of poly A to the newly formed 3' end. The AGTAAA hexanucleotide which is seen 5' of the poly A tail on the HD 12 cDNA would be predicted to have significantly less (~30%) efficacy in affecting cleavage and subsequent addition of poly A compared to mRNA with the complete sequence AATAAA and yet for most issues excluding brain this appears to be the predominantly used signal. The hexanucleotide ATTAAA which is seen 5' to the poly A of the larger cDNA (HD 14) is predicted to more efficient relative to AGTAAA but also would be predicted to have less (~70%) efficacy for processing and addition of poly A to the newly formed 3' end than the consensus sequence.

The relative abundance of the two mRNA species varies in different tissues with the larger 13.7 kb transcript predominant in adult and fetal brain. The smaller 10.3 kb transcript is the predominant mRNA species in other tissues as well as in a number of cell lines. The cause for these differences is unknown but suggests preferential tissue specific selection of a polyadenylation site or alternatively tissue specific effects on the stability of each mRNA species.

EXAMPLE 5—General Methods

The general techniques used in extracting the genome, preparing and probing a cDNA library, sequencing clones, constructing expression vectors, transforming cells, and performing immunological assays and the like, are known in the art and laboratory manuals are available describing those techniques. However, as a general guide, the following sets forth some more specific information with respect to the above.

1. Host & Control Sequences

Both prokaryotic and eukaryotic systems and their viruses may be used to express the HD encoding sequences; for example, prokaryotes may be represented by various strains of *E. coli,* Bacillus or Pseudomonas. Eukaryotic hosts include yeast and mammalian cells in culture systems. Yeast compatible vectors employing, for example, the 3 μ origin of replication of Brach, J. R. *Meth. Enz.* (1983) 101:307, or other yeast compatible origins of replications (see, for example, Stinchcomb, et al. *Nature* (1979) 282:39, and Clarke, L., et al. *Meth. Enz.* (1983) 101:300) may be used which will result in incorporation of an appropriate fragment into the host cell genome. Control sequences for yeast promoters for the synthesis of glycolytic enzymes including the promoterfor 3 phosphoglycerate kinase (Hintzeman et al., *J. Biol. Chem.* (1980) 255:2073) may be employed.

It is also, of course, possible to express genes encoding polypeptides in eukaryotic host cell cultures derived from multicellular organisms. Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral (1978), Rous sarcoma virus (RSV), adenovirus (ADV), and bovine papilloma virus (BPV). Mammalian cells may also require terminator sequences and poly A addition sequences; enhancer sequences which increase expression may also be included, and sequences which cause amplification of the gene may also be desirable. These sequences are known in the art. Vectors suitable for replication in mammalian cells may include viral replicons, or sequences which insure integration of the appropriate sequences encoding NANBV epitope into the host genome.

2. Transformations

Transformation may be by any known method for introducing polynucleotides into a host cell, including, for example, packaging the polynucleotide in a virus and transducing a host cell with the virus, and by direct uptake of the polynucleotide. The transformation procedure depends upon the host to be transformed.

3. Vector Construction

Vector construction employs standard ligation and restriction techniques which are known in the art. Isolated plasmids, DNA sequences, or synthesized oligonucleotides are cleaved, tailored and religated in the form desired.

Site-specific DNA cleavage is performed by treating with suitable restriction enzyme under conditions which generally are specified by the manufacturer of these commercially available enzymes. In general, about 1 microgram of plasmid or DNA sequence is cleaved by 1 unit of enzyme in about 20 microliters buffer solution by incubation of 1–2 hrs at 37° C. After incubation with the restriction enzyme, protein is removed by phenol/chloroform extraction and the DNA recovered by precipitation using polyacrylamide or agarose gel electrophoresis techniques, according to the general procedures found in Methods in Enzymology (1980) 65:499–560.

Sticky ended cleavage fragments may be blunt ended using *E. coli* DNA polymerase I (Klenow) in the presence of the appropriate deoxynucleotide triphosphates (dNTPs) present in the mixture. Treatment with S1 nuclease may also be used, resulting in the hydrolysis of any single stranded DNA portions.

Ligations are carried out using standard buffer and temperature conditions using T4 DNA ligase and ATP; sticky end ligations require less ATP and less ligase than blunt end ligations. When vector fragments are used as part of the ligation mixture, the vector fragment is often treated with bacterial alkaline phosphates (BAP) or calf intestinal alkaline phosphatase to remove the 5'-phosphate and thus prevent religation of the vector; alternatively, restriction enzyme digestion of unwanted fragments can be used to prevent ligation.

Ligation mixtures are transformed into suitable cloning hosts, such as *E. coli,* and successful transformants selected by, for example, antibiotic resistance, and screened for the correct construction.

4. Construction of Desired DNA Sequences

Synthetic oligonucleotides may be prepared using an automated oligonucleotide synthesizer as described by Warner (1984). If desired the synthetic strands may be labelled with $^{32}$P-ATP, using standard conditions for the reaction.

DNA sequences, including those isolated from cDNA libraries, may be modified by known techniques, including, for example site directed mutagenesis, as described by Zoller (1982). Briefly, the DNA to be modified is packaged into a phage as a single stranded sequence, and converted to a double stranded DNA with DNA polymerase using, as a primer, a synthetic oligonucleotide complementary to the portion of the DNA to be modified, and having the desired modification included in its own sequence. The resulting double stranded DNA is transformed into a phage supporting host bacterium. Cultures of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labelled synthetic probe at temperatures and conditions which permit hybridization with the correct strand, but not with the unmodified sequence. The sequences which have been identified by hybridization are recovered and cloned.

5. Hybridization with Probe

There are simple procedures well known in the art in which probes may be synthesized. The usual technique is to use a highly labelled radioactive probe of RNA or DNA, whose hybridization with the gene is assayed by autoradiography (Levin et al., Genes III, 1987 John Wiley & Sons, 359).

In view of the preferential expression of the larger 13.7 kb mRNA transcript in the human brain, a suitable antisense RNA or DNA may be used to block expression of either the larger 13.7 kb transcript or expression of the shorter 10.3 kb transcript. Preferential expression of one over the other in controlling brain tissue damage due to HD may be provided.

Although preferred embodiments of the invention are described herein in detail, it will be understood by those skilled in the art that variations may be made thereto without departing from the spirit of the invention or the scope of the appended claims.

TABLE 1

| cDNA | Size (bp) | Corresponding nucleotides within α-adducin |
|---|---|---|
| cD501 | 536 | 2820-3356 |
| cD504 | 262 | 2830-3092 |
| cD506 | 917 | 2995-3912 |
| cD507 | 278 | 2830-3108 |
| cD509 | 380 | 3532-3912 |
| cD108 | 395 | 3525-3920 |

Adducin cDNAs derived by gene tracking. The size of the cDNA is shown as well as the nucelotide sequence according to the numbering of erthrocyte α-adducin.

TABLE 2

| PRIMER SETS | PRIMER SEQUENCE | PCR CONDITIONS | | (MgCl$_2$) | SIZE (bp) |
|---|---|---|---|---|---|
| ADU 133 | AGGAACCTAGAAAGATTGTACAATG | 94°, 60s; 61°, 60s; 72°, 60s | 35 cycles | 1.5 mM | 1224 |
| ADU 1357 | TCTCAGAGCAGGGTATCGATAAG | | | | |
| ADU 1111 | TAACCTTGTGGTTGCCTGTGAGATC | 94°, 30s; 66°, 30s; 72°, 45s | 35 cycles | 1.5 mM | 504 |
| ADU 1615 | GTTAGGGACAGCAGAGGTGGAAG | | | | 597 |
| ADU 1524 | CCGAGGAAGGGCAGAATGGAAG | 94°, 30S; 65° 30s; 72°, 30s | 35 cycles | 1.5 mM | 481 |
| ADU 2005 | CTTGATGGGAGTGCTGGGAGGC | | | | 574 |
| ADU 1912 | TGAAGAGAATCTGGACGAGGCTAG | 94°, 45s; 62°, 30s; 72°, 45s | 35 cycles | 1.0 mM | 544 |
| ADU 2456 | CCATTACACAAGGACAGAGCACAG | | | | 578 |
| ADU 2162 | CCCACTGAGGCCCCTACTGAG | 94°, 30s; 68°, 30s, 72°, 30s | 35 cycles | 1.5 mM | 221 |
| ADU 2383 | GTTAGCGCAGGGCTTTCAGGAG | 4% formamide | | | |
| ADU 2354 | AAGAGTGACTCCTGAAAGCCCTG | 94°, 60s; 60°, 60s; 72°, 60s | 35 cycles | 1.0 mM | 473 |
| ADU 2827 | GATCACTGAGCAGAGAGAATGCC | | | | |
| ADU 2645 | AAGGTACTGAAGGCTTCTGCAGC | 94°, 30s; 65°, 30s; 72°, 30s | 35 cycles | 2.0 mM | 596 |
| ADU 3241 | AGTTAAGGTGAGAACAGTCCCCTGA | | | | |
| ADU 3131 | TCGACTGTGAACGTGAATAGGC | 94°, 60s, 61°, 60s, 72°, 60s | 35 cycles | 1.5 mM | 743 |
| ADU 3874 | GTTACACTGGAGAAAGGACTTCAG | | | | |

Sequence of overlapping primer sets and conditions employed to amplify α-adducin cDNA. Primer orientation is shown from 5' to 3'. Fragment sizes generated from each primer pair are shown. Two fragment sizes indicated for three sets represent the products of normal and alternately spliced exons at positions 1567 and 2015 of the brain α-adducin gene.

TABLE 3

| | GT | Clone Size (bp) | EcoRI Frag Sizes | RNA Hybridization Size and Distribution | Sequence Analysis |
|---|---|---|---|---|---|
| BIN 1A | 168 | ~650 | 7.0 | 5.5 kb: W, Fl, C, B, Co | DB similarity, 8.1e-6, HUMPHPLA2 (phospholipase A2 mRNA) |
| BIN 1B | 67 | ~600 | 12.0 | absent | DB similarity, 7.2e-5, MITGTRN6 (yeast mitochondrion) |
| | 71 | 912 | 12.0 | absent | Same as GT67 |
| | 65 | 207 | 2.9 | absent | DB search neg. |
| | 69 | 976 | 3.8 | absent | DB search neg. MER3c repeat, 12 bpGT repeat |
| | 68 | 573 | 9.5 | absent | DB search neg. L1 and MER12 repeats |
| | 167 | ~500 | 9.5 | absent | DB search neg. Sequence overlaps with GT68 |
| | 86 | ~600 | 9.0 | | DB search neg. Sequence overlaps with GT68 |
| | 166 | ~550 | 12.0 | 4.5 kb: similar to GT88 | Not sequenced |
| | 88 | ~600 | 6.0 | 4.5 kb: similar to GT 166 | Not sequenced |
| | 149 | 584 | 6.0, 5.0 | 10 kb, 12 kb: K, Co, Fi, L, W, C | DB search neg. Coding Potential Excellent, Predicted exon. |

TABLE 3-continued

| | GT | Clone Size (bp) | EcoRI Frag Sizes | RNA Hybridization Size and Distribution | Sequence Analysis |
|---|---|---|---|---|---|
| BIN 2 | 66 | 644 | 10.0 | absent | DB search neg. |
| | 165 | 600; 550 | 11.5, 4.2 | absent | DB search neg. Sequence overlaps with GT66 |
| | 87 | 536 | 8.5 | absent | DB search neg. |
| | 70 | 757 | 9.0, 8.5, 1.2 | 10.0, 12.0 kb,: L, F, C, W, B | DB search neg. Coding potential excellent |
| | 63 | 600 | 9.0, 1.2 | ND | Not sequenced |
| | 54 | 757 | 2.7 | absent | DB search neg. ALU and MER18 repeats |
| | 72 | 764 | 2.8 | absent | DB search neg. |
| | 189 | 695; 578 | 11.0, 6.0 | | DB search neg. 2 partial ALU repeats, composite clone |
| BIN 3A | 23 | 551 | 14.0 | absent | DB search neg. MIRc repeat. |
| BIN 3B | 49 | 592 | 14.0 | | See GT23 |
| | 90 | 532 | 14.0 | absent | See GT23 |
| | 93 | 595 | 14.0 | | See GT23 |
| | 129 | 589 | | | See GT23 |
| | 130 | 597 | | | See GT23 |
| | 136 | ~500 | 14.0, 7.5 | absent | Not sequenced |
| | 44 | 646 | 13.7 | absent | DB search neg. |
| | 48 | 550 | 14.0 | absent | DB search neg. |
| | 45 | 516 | 9.0 | 3.8 kb: W, L, F, C, Co | DB search neg. 2 large ORF, coding potential excellent |
| | 34b | ~500 | | | |
| | 172 | 560 | 5.0 | ND | DB search neg. Sequence overlaps with GT45 |
| | 167 | ~500 | 6.4 | absent | Not sequenced. |
| | 48 | 490 | 13.0 | 4.0 kb: Adducin | |
| | 50 | ~600 | 15.0 | 4.0 kb: Adducin | |
| | 171 | ~500 | 7.0 | 4.0 kb: Adducin | |
| | 173 | ~560 | 14.0, 2.8, 0.5 | 4.0 kb: Adducin | |
| | 174 | ~450 | 10.0, 5.2 | 4.0 kb: Adducin | |
| | 24 | ~600 | 15.0, 7.8, 6.0 | 12.0 kb | DB search neg. 307 bp similar to LI repeat. |
| | 30 | 458 | 6.0 | | DB search neg. ALU repeat |
| | 138 | ~600 | 13.0 | absent | DB similarity, 4.2e-4, HSILIAG, Alu repeat present |
| | 169 | ~550 | 8.0, 14.0 | ND | DB search neg. 43 bp of Alu present |
| | 127 | 550 | 16.0, 14.0, 7.5 | absent | DB search neg. Sequence overlap with GT169 |
| | 170 | | 14.0 | absent | Not sequenced. |
| | 53 | ~550 | 16.0 | absent | DB search neg. 182 bp of L1 repeat |
| BIN4 | 128 | 480 | 14.0 | absent | DB search neg |
| | 131 | 422 | 12.0.11.0 | 5.5 kb | DB similarity 7.4e-5,TFD:P01136.422 bp ORF. Coding potential excellent |
| | 164 | 443:250 | | 5.5 kb | DB search neg. 443 bp ORF. Coding potential excellent. Composite clone |
| | 154 | 439 | 11.0.9.0.4.2 | 5.5 kb | DB search neg. 439 bp ORF. Coding potential excellent |
| | 159 | 400 | 11.0 | | DB search neg. Coding potential good |
| | 43 | 495 | 6.0 | absent | DB search neg. 495 bp ORF. coding potential |
| | 133 | 480 | 14.0.18.0 | absent | DB search neg. |
| BIN 3A | 98 | 450 | 14.0.9.0 | 3.6 kb: wide distribution | Not sequenced |
| BIN 5b | | | | | |
| | 123 | 447 | 14.0.9.0.4.1 | 1.8,3.6 kb: FI, L, W, C, C o | DB search neg. Large ORF with good coding potential. 221 bp overlap with GT128 |
| | 126 | 352 | 14.0.9.0 | ND | DB similarity of low significance (5.0e-5,SP:RA18 YEAST) |
| | 125 | 662 | 7.5 | absent | DB search neg. |
| | 137 | 500 | 9.0 | absent | DB search neg. |
| | 160 | ~500 | 4.2 | absent | DB search neg (partial sequence). 179 bp ORF. Coding potential good. |
| | 161 | 349 | 9.0 | 3.8 kb: | DB match, 3.3e-102,HUMXT01095 (EST) is identical |

Table 3 Legend
Summary of characterization of 58 retrieved cDNA fragments. The clones are listed by name (as GTnos.) according to their physical intervals or BINs assignment YAC clones. The sizes of the cDNA fragments are given in base pairs. The genomic fragments detected with these clones in human and yeast DNAs digested with EcoRI are also listed. Sizes of mRNAs detected in the tissues are given in kilobases from K—Kidney, Co—Cos cells, Fi—fibroblasts, L—lymphoblast, W—HL-60 cells, C—Cacp-2 cells, B—bone marrow, F—frontal cortex, FB—fetal brain. Groups of clones that are shown bracketed indicate those that partially overlap as determined by cross hybridization or sequence analysis. Database (DB) searches were carried out against non-redundant nucleic acid and protein databases of NCBI, as well as the dbEST and Transcription Factor databases. Characterized repeat sequences were edited prior to BLAST searches. All database marches with BLAST expectation values less than $1 \times 10^{-4}$ are reported, but similarities greater than $10^{-10}$ were considered borderline. Coding potential was judged by the GRAIL e-mail server and potential exons were identified using the SORFIND program. Human repeat sequences were identified by the PYTHIA e-mail server.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 105 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
        ( A ) CHROMOSOME/SEGMENT: 4p16.3
        ( B ) MAP POSITION: 1362
        ( C ) UNITS: bp ( x i ) SEQUENCE DESCRIPTION: SEQ ID NO:1:

```
ACTAAGCTGT GGACGAACAT TACACACGAT CACGTGAAAC CCTTGCTGCA GTCTCTCTCG        60

TCCGGTGTCT GCGTGCCAAG CTGTATTACC AACTGCTTGT GGACT                       105
```

( 2 ) INFORMATION FOR SEQ ID NO:2:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:2:

```
Thr Lys Val Trp Thr Asn Ile Thr His Asp His Val Lys Pro Leu Leu
 1               5                  10                      15

Gln Ser Leu Ser Ser Gly Val Cys Val Pro Ser Cys Ile Thr Asn Cys
            20              25              30

Leu Trp Thr
        35
```

( 2 ) INFORMATION FOR SEQ ID NO:3:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
        ( A ) CHROMOSOME/SEGMENT: 4p16.3
        ( B ) MAP POSITION: 2010
        ( C ) UNITS: bp ( x i ) SEQUENCE DESCRIPTION: SEQ ID NO:3:

GAGGAAGGAG ACGGATGCGC TAGAGAGTAC CTGTTACCCT AACCTTGT         48

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:4:

Gly Asp Gly Cys Ala Arg Glu Tyr Leu Leu Pro
1               5                   10

( 2 ) INFORMATION FOR SEQ ID NO:5:

( i ) SEQUENCE CHARACTERISTICS:
        ( A ) LENGTH: 380 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
        ( A ) CHROMOSOME/SEGMENT: 4p16.3
        ( C ) UNITS: bp ( x i ) SEQUENCE DESCRIPTION: SEQ ID NO:5:

AATTTCTTCT TGTTTAAGAG TATGCTGGCC GGGCGCGGTG GCTCACGCCT GTAATCCCAG         60
CACTTTGGGA GGCCGAGGCG GGTGGATCAT GAGGTCAGGA GATCGAGACC ATCCTGGCTA        120
ACAAGGTGAA ACCCCGTCTC TACTAAAAAT ACAAAAAATT AACCGGGCGC GGTGGCGGGC        180
GCCTGTAGTC CCAGCTACTC GGGAGGCTGA GGCAGGAGAA TGGCGTGAAC CCGGGAAGCG        240
GAGCTTTCAG TGAGCCGAGA TTGCGCCACT GCAGTCCGCA GTCCGGCCTG GGCGACAGAG        300
CAAGACTCCG TCTCAAAAAA AAAAAAAAAA AAAAAAAAAA AAAAAAAGA GTATGCTGAT         360
TGATATTTGT TCATCATGGG                                                    380

( 2 ) INFORMATION FOR SEQ ID NO:6:

( i ) SEQUENCE CHARACTERISTICS:
        ( A ) LENGTH: 757 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( B ) CLONE: Clone GT70

( v i i i ) POSITION IN GENOME:
        ( A ) CHROMOSOME/SEGMENT: 4p16.3
        ( C ) UNITS: bp ( x i ) SEQUENCE DESCRIPTION: SEQ ID NO:6:

| | | | | | | |
|---|---|---|---|---|---|---|
| AAAGGAAATT | AAAAAGAATG | GTGCCCCTCG | GAGTTTGCGA | GCTGCCCTGT | GGAGGTCTGC | 60 |
| TGAGCTGGCT | CACCTGGTTC | GGCCTCAGAA | ATGCAGGCCT | TACCTGGTGA | ACCTTCTGCC | 120 |
| GTGCCTGACT | CGAACAAGCA | AGAGACCCGA | AGAATCAGTC | CAGGAGACCT | TGGCTGCAGC | 180 |
| TGTTCCCAAA | ATTATGGCTT | CTTTTGGCAT | TTGCAAATGA | CAATGAAAGG | TTGTTAAAGG | 240 |
| CCTTCATAGC | GAACTGAAGT | CAAGCNNCCC | CCACCATTCG | GCGGACAGCG | GCTGGATCAG | 300 |
| CAGTGAGCAT | CTGCCAGCAC | TCAAGAAGGA | CACAATATTT | CTATAGTTGG | CTACTAAATG | 360 |
| TGCTCTTAGG | CTTCGCGTTC | CTGTCGAGGA | TGAACACTCC | ACNTGCTGAT | TCTTGGCGTG | 420 |
| CTGCTCACCT | TGAGGTATTT | GGTGCCCTTG | CTGCAGCAGC | AGGTCAAGGA | CACAAGCCTG | 480 |
| AAAGGAGTCT | TCGGAGTGAC | AAGGAAAGAA | AGGAAGTCTC | TCCTTCTGCA | GAGCACTTGA | 540 |
| TCCAGGTTTA | TGAACTGACG | TTACATGATA | CACAGCACCA | AGACCACAAT | GTTGTGACCG | 600 |
| GAGCCCTGGA | GCTGTTGCAG | CAGCTCTTCA | GAACGCCTCC | ACCCGAGCTT | CTGCAAACCC | 660 |
| TGACCGCAGT | CGGGGGCATT | GGCAGGCTCA | CCGCTGCTAA | GGAGGAGTCT | GGTGGCCGAA | 720 |
| GCCGTAGTGG | GAGTATTGTG | GAACTTATAG | CTGGAGG | | | 757 |

( 2 ) INFORMATION FOR SEQ ID NO:7:

( i ) SEQUENCE CHARACTERISTICS:
        ( A ) LENGTH: 584 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( B ) CLONE: Clone:GT149

( v i i i ) POSITION IN GENOME:
        ( A ) CHROMOSOME/SEGMENT: 4p16.3
        ( C ) UNITS: bp ( x i ) SEQUENCE DESCRIPTION: SEQ ID NO:7:

| | | | | | | |
|---|---|---|---|---|---|---|
| GGCCATTTTG | AGGGTTCTGA | TTTCCCAGTC | AACTGAAGAT | ATTGTTCTTT | CTCGTATCAG | 60 |
| GAGCTCTTCT | TCTCTCCGTA | TTTAACTCCT | GTACAGTAAT | TAATAGGTTA | AGAGATGGGG | 120 |
| ACAGTACTTC | AACNCTAGAA | GAACACAGTG | AAGGGAAACA | AATAAAGAAT | TTGCCAGAAG | 180 |
| AAACATTTTC | AAGGTTTCTA | TTACAACTGG | TTGGTATCTT | TTAGAAGACA | TTGTTACAAA | 240 |
| ACAGCTGAAG | GGTGGGAAAT | GAGTGAGCAG | CAACATACTT | TTTATTGCCA | GGAACTAAGG | 300 |
| CACACTGCTA | ACGTGTCTGA | TCCACATCTT | CAAGTCTGGA | ATGTTCCGGA | GAATCACAGC | 360 |
| AGCTGCCACT | AGGCTGTTCC | GCAGTGATGG | CTGTGGCGGC | AGTTTCTACA | CCCTGGACAG | 420 |
| CTCGAACTTG | CGGGCTCGTT | CCATGATCAC | CACCCACCCG | GCCCTGGTGC | TGCTCTGGTG | 480 |
| TCAGATACTG | CTGCTTGTGA | AGGAGACCGA | CTACCGCTGG | TGGGCAGAAG | TGCAGCAGAC | 540 |
| CCCGAAAAGA | CACAGTCTGT | CCAGCACAAA | GTTACTTAGC | CCAC | | 584 |

( 2 ) INFORMATION FOR SEQ ID NO:8:

( i ) SEQUENCE CHARACTERISTICS:
        ( A ) LENGTH: 4032 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i i ) POSITION IN GENOME:
  ( A ) CHROMOSOME/SEGMENT: 4p16.3
  ( B ) MAP POSITION: 9677
  ( C ) UNITS: bp ( x i ) SEQUENCE DESCRIPTION: SEQ ID NO:8:

| | | | | | | |
|---|---|---|---|---|---|---|
| GCAGCCCCAG | GAAGCCCATA | TCACCGGCTG | CTGACTTGTT | TACGAAATGT | CCACAAGGTC | 60 |
| ACCACCTGCT | GAGCGCCATG | GTGGGAGAGA | CTGTGAGGCG | GCAGCTGGGG | CCGGAGCCTT | 120 |
| TGGAAGTCTG | TGCCCTTGTG | CCCTGCCTCC | ACCGAGCCAG | CTTGGTCCCT | ATGGGCTTCC | 180 |
| GCACATGCCG | CGGGCGGCCA | GGCAACGTGC | GTGTCTCTGC | CATGTGGCAG | AAGTGCTCTT | 240 |
| TGTGGCAGTG | GCCAGGCAGG | GAGTGTCTGC | AGTCCTGGTG | GGGCTGAGCC | TGAGGCCTTC | 300 |
| CAGAAAGCAG | GAGCAGCTGT | GCTGCACCCC | ATGTGGGTGA | CCAGGTCCTT | TCTCCTGATA | 360 |
| GTCACCTGCT | GGTTGTTGCC | AGGTTGCAGC | TGCTCTTGCA | TCTGGGCCAG | AAGTCCTCCC | 420 |
| TCCTGCAGGC | TGGCTGTTGG | CCCCTCTGCT | GTCCTGCAGT | AGAAGGTGCC | GTGAGCAGGC | 480 |
| TTTGGGAACA | CTGGCCTGGG | TCTCCCTGGT | GGGGTGTGCA | TGCCACGCCC | CGTGTCTGGA | 540 |
| TGCACAGATG | CCATGGCCTG | TGCTGGGCCA | GTGGCTGGGG | GTGCTAGACA | CCCGGCACCA | 600 |
| TTCTCCCTTC | TCTCTTTTCT | TCTCAGGATT | TAAAATTTAA | TTATATCAGT | AAAGAGATTA | 660 |
| ATTTTAACGT | AACTCTTTCT | ATGCCCGTGT | AAAGTATGTG | AATCGCAAGG | CCTGTGCTGC | 720 |
| ATGCGACAGC | GTCCGGGGTG | GTGGACAGGG | CCCCCGGCCA | CGCTCCCTCT | CCTGTAGCCA | 780 |
| CTGGCATAGC | CCTCCTGAGC | ACCCGCTGAC | ATTTCGTTG | TACATGTTCC | TGTTTATGCA | 840 |
| TTCACAAGGT | GACTGGGATG | TAGAGAGGCG | TTAGTGGGCA | GGTGGCCACA | GCAGGACTGA | 900 |
| GGACAGGCCC | CCATTATCCT | AGGGGTGCGC | TCAACTGCAG | CCCCTCCTCC | TCGGGCACAG | 960 |
| ACGACTGTCG | TTCTCCACCC | ACCAGTCAGG | GACAGCAGCC | TCCCTGTCAC | TCAGCTGAGA | 1020 |
| AGGCCAGCCC | TCCCTGGCTG | TGAGCAGCCT | CCACTGTGTC | CAGAGACATG | GGCCTCCCAC | 1080 |
| TCCTGTTCCT | TGCTAGCCCT | GGGGTGGCGT | CTGCCTAGGA | GCTGGCTGGC | AGGTGTTGGG | 1140 |
| ACCTGCTGCT | CCATGGATGC | ATGCCCTAAG | AGTGTCACTG | AGCTGTGTTT | TGTCTGAGCC | 1200 |
| TCTCTCGGTC | AACAGCAAAG | CTTGGTGTCT | TGGCACTGTT | AGTGACAGAG | CCCAGCATCC | 1260 |
| CTTCTGCCCC | CGTTCCAGCT | GACATCTTGC | ACGGTGACCC | CTTTTAGTCA | GGAGAGTGCA | 1320 |
| GATCTGTGCT | CATCGGAGAC | TGCCCCACGG | CCCTGTCAGA | GCCGCCACTC | CTATCCCCAG | 1380 |
| GACAGGTCCC | TGGACCAGCC | TCCTGTTTGC | AGGCCCAGAG | GAGCCAAGTC | ATTAAAATGG | 1440 |
| AAGTGGATTC | TGGATGGCCG | GGCTGCTGCT | GATGTAGGAG | CTGGATTTGG | GAGCTCTGCT | 1500 |
| TGCCGACTGG | CTGTGAGACG | AGGCAGGGGC | TCTGCTTCCT | CAGCCCTAGA | GGCGAGCCAG | 1560 |
| GCAAGGTTGG | CGACTGTCAT | GTGGCTTGGT | TTGGTCATGC | CCGTCGATGT | TTTGGGTATT | 1620 |
| GAATGTGGTA | AGTGGAGGAA | ATGTTGGAAC | TCTGTGCAGG | TGCTGCCTTG | AGACCCCAA | 1680 |
| GCTTCCACCT | GTCCCTCTCC | TATGTGGCAG | CTGGGAGCA | GCTGAGATGT | GGACTTGTAT | 1740 |
| GCTGCCCACA | TACGTGAGGG | GGAGCTGAAA | GGGAGCCCCT | GCTCAAAGGG | AGCCCCTCCT | 1800 |
| CTGAGCAGCC | TCTGCCAGGC | CTGTATGAGG | CTTTTCCCAC | CAGCTCCCAA | CAGAGGCCTC | 1860 |
| CCCCAGCCAG | GACCACCTCG | TCCTCGTGGC | GGGGCAGCAG | GAGCGGTAGA | AAGGGGTCCG | 1920 |
| ATGTTTGAGG | AGGCCCTTAA | GGGAAGCTAC | TGAATTATAA | CACGTAAGAA | AATCACCATT | 1980 |

```
CTTCCGTATT GGTTGGGGGC TCCTGTTTCT CATCCTAGCT TTTTCCTGGA AAAGCCCGCT      2040
AGAAGGTTTG GGAACGAGGG GAAAGTTCTC AGAACTGTTG CTGCTCCCCA CCCGCCTCCC      2100
GCCTCCCCCG CAGGTTATGT CAGCAGCTCT GAGACAGCAG TATCACAGGC AGATGTTGT       2160
TCCTGGCTAG ATGTTTACAT TTGTAAGAAA TAACACTGTG AATGTAAAAC AGAGCCATTC      2220
CCTTGGAATG CATATCGCTG GGCTCAACAT AGAGTTTGTC TTCCTCTTGT TTACGACGTG      2280
ATCTAAACCA GTCCTTAGCA AGGGGCTCAG AACACCCCGC TCTGGCAGTA GGTGTCCCCC      2340
ACCCCCAAAG ACCTGCCTGT GTGCTCCGGA GATGAATATG AGCTCATTAG TAAAAATGAC      2400
TTCACCCACG CATATACATA AAGTATCCAT GCATGTGCAT ATAGACACAT CTATAATTTT      2460
ACACACACAC CTCTCAAGAC GGAGATGCAT GGCCTCTAAG AGTGCCCGTG TCGGTTCTTC      2520
CTGGAAGTTG ACTTTCCTTA GACCCGCCAG GTCAAGTTAG CCGCGTGACG GACATCCAGG      2580
CGTGGGACGT GGTCAGGGCA GGGCTCATTC ATTGCCCACT AGGATCCCAC TGGCGAAGAT      2640
GGTCTCCATA TCAGCTCTCT GCAGAAGGGA GGAAGACTTT ATCATGTTCC TAAAAATCTG      2700
TGGCAAGCAC CCATCGTATT ATCCAAATTT TGTTGCAAAT GTGATTAATT GGTTGTCAA       2760
GTTTTGGGGG TGGGCTGTGG GGAGATTGCT TTTGTTTTCC TGCTGGTAAT ATCGGGAAAG      2820
ATTTTAATGA AACCAGGGTA GAATTGTTTG GCAATGCACT GAAGCGTGTT TCTTTCCCAA      2880
AATGTGCCTC CCTTCCGCTG CGGGCCCAGC TGAGTCTATG TAGGTGATGT TTCCAGCTGC      2940
CAAGTGCTCT TTGTTACTGT CCACCCTCAT TTCTGCCAGC GCATGTGTCC TTTCAAGGGG      3000
AAAATGTGAA GCTGAACCCC CTCCAGACAC CCAGAATGTA GCATCTGAGA AGGCCCTGTG      3060
CCCTAAAGGA CACCCCTCGC CCCCATCTTC ATGGAGGGGG TCATTTCAGA GCCCTCGGAG      3120
CCAATGAACA GCTCCTCCTC TTGGAGCTGA GATGAGCCCC ACGTGGAGCT CGGGACGGAT      3180
AGTAGACAGC AATAACTCGG TGTGTGGCCG CCTGGCAGGT GGAACTTCCT CCCGTTGCGG      3240
GGTGGAGTGA GGTTAGTTCT GTGTGTCTGG TGGGTGGAGT CAGGCTTCTC TTGCTACCTG      3300
TGAGCATCCT TCCCAGCAGA CATCCTCATC GGGCTTTGTC CCTCCCCCGC TTCCTCCCTC      3360
TGCGGGGAGG ACCCGGGACC ACAGCTGCTG GCCAGGGTAG ACTTGGAGCT GTCCTCCAGA      3420
GGGGTCACGT GTAGGAGTGA GAAGAAGGAA GATCTTGAGA GCTGCTGAGG GACCTTGGAG      3480
AGCTCAGGAT GGCTCAGACG AGGACACTCG CTTGCCGGGC CTGGCCCTCC TGGGAAGGAG      3540
GGAGCTGCTC AGAATGCCGC ATGACAACTG AAGGCAACCT GGAAGGTTCA GGGCCCGCTC      3600
TTCCCCCATG TGCCTGTCAC GCTCTGGTGC AGTCAAAGGA ACGCCTTCCC CTCAGTTGTT      3660
TCTAAGAGCA GAGTCTCCCG CTGCAATCTG GGTGGTAACT GCCAGCCTTG GAGGATCGTG      3720
GCCAACGTGG ACCTGCCTAC GGAGGGTGGG CTCTGACCCA AGTGGGGCCT CCTTGCCCAG      3780
GTCTCACTGC TTTGCACCGT GGTCAGAGGG ACTGTCAGCT GAGCTTGAGC TCCCCTGGAG      3840
CCAGCAGGGC TGTGATGGGC GAGTCCCGGA GCCCACCCA GACCTGAATG CTTCTGAGAG       3900
CAAAGGGAAG GACTGACGAG AGATGTATAT TTAATTTTTT AACTGCTGCA AACATTGTAC      3960
ATCCAAATTA AAGGGAAAAA ATGGAAACCA TCAAAAAAAA AAAAAAAAAA AAAAAAAAA       4020
AAAAAAAAAA AA                                                         4032
```

( 2 ) INFORMATION FOR SEQ ID NO:9:

( i ) SEQUENCE CHARACTERISTICS:
        ( A ) LENGTH: 688 base pairs
        ( B ) TYPE: nucleic acid
        ( C ) STRANDEDNESS: single
        ( D ) TOPOLOGY: linear ( i i ) MOLECULE TYPE: cDNA (i i i) HYPOTHETICAL: NO (i v) ANTI-SENSE: NO (v i i i) POSITION IN GENOME:
  (A) CHROMOSOME/SEGMENT: 4p16.3
  (B) MAP POSITION: 9677
  (C) UNITS: bp (x i) SEQUENCE DESCRIPTION: SEQ ID NO:9:

| | | | | | | |
|---|---|---|---|---|---|---|
| GCAGCCCCAG | GAAGCCCATA | TCACCGGCTG | CTGACTTGTT | TACGAAATGT | CCACAAGGTC | 60 |
| ACCACCTGCT | GAGCGCCATG | GTGGGAGAGA | CTGTGAGGCG | GCAGCTGGGG | CCGGAGCCTT | 120 |
| TGGAAGTCTG | TGCCCTTGTG | CCCTGCCTCC | ACCGAGCCAG | CTTGGTCCCT | ATGGGCTTCC | 180 |
| GCACATGCCG | CGGGCGGCCA | GGCAACGTGC | GTGTCTCTGC | CATGTGGCAG | AAGTGCTCTT | 240 |
| TGTGGCAGTG | GCCAGGCAGG | GAGTGTCTGC | AGTCCTGGTG | GGGCTGAGCC | TGAGGCCTTC | 300 |
| CAGAAAGCAG | GAGCAGCTGT | GCTGCACCCC | ATGTGGGTGA | CCAGGTCCTT | TCTCCTGATA | 360 |
| GTCACCTGCT | GGTTGTTGCC | AGGTTGCAGC | TGCTCTTGCA | TCTGGGCCAG | AAGTCCTCCC | 420 |
| TCCTGCAGGC | TGGCTGTTGG | CCCCTCTGCT | GTCCTGCAGT | AGAAGGTGCC | GTGAGCAGGC | 480 |
| TTTGGGAACA | CTGGCCTGGG | TCTCCCTGGT | GGGGTGTGCA | TGCCACGCCC | CGTGTCTGGA | 540 |
| TGCACAGATG | CCATGGCCTG | TGCTGGGCCA | GTGGCTGGGG | GTGCTAGACA | CCCGGCACCA | 600 |
| TTCTCCCTTC | TCTCTTTTCT | TCTCAGGATT | TAAAATTTAA | TTATATCAGT | AAAGAGATTA | 660 |
| ATTTTAACGT | AAAAAAAAAA | AAAAAAAA | | | | 688 |

(2) INFORMATION FOR SEQ ID NO:10:

(i) SEQUENCE CHARACTERISTICS:
    (A) LENGTH: 23 amino acids
    (B) TYPE: amino acid
    (C) STRANDEDNESS: single
    (D) TOPOLOGY: linear (i i) MOLECULE TYPE: protein (i i i) HYPOTHETICAL: NO (i v) ANTI-SENSE: NO (v) FRAGMENT TYPE: C-terminal (x i) SEQUENCE DESCRIPTION: SEQ ID NO:10:

```
Ala  Ala  Pro  Gly  Ser  Pro  Tyr  His  Arg  Leu  Leu  Thr  Cys  Leu  Arg  Asn
 1              5                        10                        15
Val  His  Lys  Val  Thr  Thr  Cys
              20
```

(2) INFORMATION FOR SEQ ID NO:11:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:11:

TCAGGGCAGG GCTCATTCAT TC                                  22

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

GATGTACAAT GTTTGCAGCA GTTA    24

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

ATGTAATTGT TCACGACATG TGGC    24

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:14:

AAATAACATC CAGAATCTTC AGAT    24

We claim:

1. A purified DNA molecule having the following sequence designated GT70:

AAAGGAAATT AAAAAGAATG GTGCCCCTCG
GAGTTTGCGA GCTGCCCTGT GGAGGTCTGC
TGAGCTGGCT CACCTGGTTC GGCCTCAGAA
ATGCAGGCCT TACCTGGTGA ACCTTCTGCC
GTGCCTGACT CGAACAAGCA AGAGACCCGA
AGAATCAGTC CAGGAGACCT GGCTGCAGC
TGTTCCCAAA ATTATGGCTT CTTTTGGCAT
TTGCAAATGA CAATGAAAGG TTGTTAAAGG
CCTTCATAGC GAACTGAAGT CAAGCGGCCC
CCACCATTCG GCGGACAGCG GCTGGATCAG
CAGTGAGCAT CTGCCAGCAC TCAAGAAGGA
CACAATATTT CTATAGTTGG CTACTAAATG
TGCTCTTAGG CTTCGCGTTC CTGTCGAGGA
TGAACACTCC ACGTGCTGAT TCTTGGCGTG
CTGCTCACCT TGAGGTATTT GGTGCCCTTG
CTGCAGCAGC AGGTCAAGGA CACAAGCCTG
AAAGGAAGTCT TCGGAGTGAC AAGGAAAGAA
AGGAAGTCTC TCCTTCTGCA GAGCACTTGA
TCCAGGTTTA TGAACTGACG TTACATGATA

```
                CACAGCACCA AGACCACAAT GTTGTGACCG

GAGCCCTGGA GCTGTTGCAG CAGCTCTTCA

GAACGCCTCC ACCCGAGCTT CTGCAAACCC

TGACCGCAGT CGGGGGCATT GGCAGGCTCA

CCGCTGCTAA GGAGGAGTCT GGTGGCCGAA

GCCGTAGTGG GAGTATTGTG GAACTTATAG

CTGGAGG.
```

2. A purified DNA molecule having the following sequence designated GT149:

```
GGCCATTTTG AGGGTTCTGA TTTCCCAGTC AACTGAAGAT ATTGTTCTTT CTCGTATCAG
GAGCTCTTCT TCTCTCCGTA TTTAACTCCT GTACAGTAAT TAATAGGTTA AGAGATGGGG
ACAGTACTTC AACGCTAGAA GAACACAGTG AAGGGAAACA AATAAAGAAT TTGCCAGAAG
AAACATTTTC AAGGTTTCTA TTACAACTGG TTGGTATCTT TTAGAAGACA TTGTTACAAA
ACAGCTGAAG GGTGGGAAAT GAGTGAGCAG CAACATACTT TTTATTGCCA GGAACTAAGG
CACACTGCTA ACGTGTCTGA TCCACATCTT CAAGTCTGGA ATGTTCCGGA GAATCACAGC
AGCTGCCACT AGGCTGTTCC GCAGTGATGG CTGTGGCGGC AGTTTCTACA CCCTGGACAG
CTCGAACTTG CGGGCTCGTT CCATGATCAC CACCCACCCG GCCCTGGTGC TGCTCTGGTG
TCAGATACTG CTGCTTGTGA AGGAGACCGA CTACCGCTGG TGGGCAGAAG TGCAGCAGAC
CCCGAAAAGA CACAGTCTGT CCAGCACAAA GTTACTTAGC CCAC.
```

3. A purified gene sequence comprising the DNA sequence of claim 1 or 2.

4. A purified DNA molecule comprising the sequence provided herein as SEQ ID NO:8.

5. A purified DNA molecule comprising the sequence of nucleotides 689–4032, inclusive, of SEQ ID NO:8.

6. A purified mRNA molecule transcribed preferentially in human brain by transcription of said DNA molecule of claim 5.

7. A purified DNA molecule comprising the cDNA associated with Huntington's Disease and having the UTR of HD 14 at its 3' untranslated end.

8. A DNA probe comprising a DNA sequence of at least 12 nucleotides selected from said sequence of claim 1.

9. A DNA probe comprising a DNA sequence of at least 12 nucleotides selected from said sequence of claim 2.

10. A DNA probe comprising a DNA sequence of at least 12 nucleotides selected from said sequence of claim 5.

11. A recombinant vector comprising a DNA sequence of claim 1.

12. A recombinant vector comprising a DNA sequence of claim 2.

13. A recombinant vector comprising a DNA sequence of claim 5.

* * * * *

UNITED STATES PATENT AND TRADEMARK OFFICE
CERTIFICATE OF CORRECTION

PATENT NO. : 5,534,438
DATED : 9 July 1996
INVENTOR(S) : Michael HAYDEN, Paul GOLDBERG, Biaoyang LIN, and Johanna M. ROMMENS It is certified that error appears in the above-indentified patent and that said Letters Patent is hereby corrected as shown below:

ON THE TITLE PAGE:
Item [75];

In the Inventors, after "Andrew" please add -- ; Biaoyang Lin --.

Column 4, line 66, after "70" please insert --(SEQ ID NO:6)-- and after "149" please insert --(SEQ ID NO:7)--.

Column 5, line 54, please correct "$4_p$" to read --4p--.

Column 7, line 12, please correct "340" to read -- 3' --.

Column 7, line 14, please correct "mounts" to read -- amounts --.

Column 9, line 56, please correct "650" to read -- 65 --.

Column 18, line 50, please correct "33306" to read -- 353G6 --.

UNITED STATES PATENT AND TRADEMARK OFFICE
CERTIFICATE OF CORRECTION

PATENT NO. : 5,534,438
DATED : 9 July 1996
INVENTOR(S) : Michael HAYDEN, Paul GOLDBERG, Biaoyang, LIN, and Johanna M. ROMMENS It is certified that error appears in the above-indentified patent and that said Letters Patent is hereby corrected as shown below:

Column 22, line 3, please correct "1-6" to read -- 1.6 --.

Signed and Sealed this

Tenth Day of June, 1997

Attest:

BRUCE LEHMAN

Attesting Officer

Commissioner of Patents and Trademarks